United States Patent
Sheldon et al.

(10) Patent No.: US 12,220,585 B2
(45) Date of Patent: *Feb. 11, 2025

(54) METHODS AND APPARATUS FOR REDUCING CURRENT DRAIN IN A MEDICAL DEVICE

(71) Applicant: Medtronic, Inc., Minneapolis, MN (US)

(72) Inventors: Todd J. Sheldon, North Oaks, MN (US); Vincent P. Ganion, Blaine, MN (US); Greggory R. Herr, Blaine, MN (US); Michael L. Hudziak, Stillwater, MN (US); Juliana E. Pronovici, New Hope, MN (US); Paul R. Solheim, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 525 days.

This patent is subject to a terminal disclaimer.

(21) Appl. No.: 17/542,328

(22) Filed: Dec. 3, 2021

(65) Prior Publication Data

US 2022/0088393 A1    Mar. 24, 2022

Related U.S. Application Data

(63) Continuation of application No. 16/681,278, filed on Nov. 12, 2019, now Pat. No. 11,207,526.
(Continued)

(51) Int. Cl.
*A61N 1/365*    (2006.01)
*A61N 1/372*    (2006.01)
*A61N 1/378*    (2006.01)

(52) U.S. Cl.
CPC ..... *A61N 1/36542* (2013.01); *A61N 1/37276* (2013.01); *A61N 1/37282* (2013.01); *A61N 1/378* (2013.01)

(58) Field of Classification Search
CPC ............ A61N 1/36535; A61N 1/36542; A61N 1/36578; A61N 1/36585; A61N 1/368;
(Continued)

(56) References Cited

U.S. PATENT DOCUMENTS

| 4,485,813 A | 12/1984 | Anderson et al. |
| 5,052,388 A | 10/1991 | Sivula et al. |

(Continued)

FOREIGN PATENT DOCUMENTS

| CN | 102971046 A | 3/2013 |
| CN | 107007933 A | 8/2017 |
| CN | 107073274 A | 8/2017 |

OTHER PUBLICATIONS (PCT/US2019/061138) PCT Notification of Transmittal of the International Search Report and the Written Opinion of the International Searching Authority, Mailed Feb. 14, 2020, 11 pages.
(Continued)

*Primary Examiner* — Allen Porter

(57) ABSTRACT

A medical device is configured to produce a cardiac motion signal by sampling a signal produced by an axis of a motion sensor, starting a blanking period, suspending the sampling of the signal during at least a portion of the blanking period, and restarting the sampling of the signal at the sampling frequency before the blanking period has expired. The medical device may detect a cardiac event from the cardiac motion signal and generate a pacing pulse in response to detecting the cardiac event in some examples.

18 Claims, 9 Drawing Sheets

Related U.S. Application Data

(60) Provisional application No. 62/767,009, filed on Nov. 14, 2018.

(58) Field of Classification Search
CPC ............... A61N 1/3682; A61N 1/3684; A61N 1/3756
See application file for complete search history.

(56) References Cited

U.S. PATENT DOCUMENTS

| | | |
|---|---|---|
| 5,507,782 A | 4/1996 | Kieval et al. |
| 5,529,578 A | 6/1996 | Struble |
| 5,593,431 A | 1/1997 | Sheldon |
| 5,720,769 A | 2/1998 | van Oort et al. |
| 5,885,471 A | 3/1999 | Ruben et al. |
| 6,044,297 A | 3/2000 | Sheldon et al. |
| 6,052,388 A | 4/2000 | Tajima et al. |
| 6,077,236 A | 6/2000 | Cunningham |
| 6,507,782 B1 | 1/2003 | Rumbo et al. |
| 6,529,578 B1 | 3/2003 | Taguchi et al. |
| 6,593,431 B2 | 7/2003 | Sheehan |
| 6,720,769 B2 | 4/2004 | Gerald, II et al. |
| 6,885,471 B1 | 4/2005 | Minowa et al. |
| 8,033,998 B2 | 10/2011 | Bullens et al. |
| 8,050,764 B2 | 11/2011 | Freeberg |
| 8,433,409 B2 | 4/2013 | Johnson et al. |
| 8,532,785 B1 | 9/2013 | Crutchfield et al. |
| 8,541,131 B2 | 9/2013 | Lund et al. |
| 9,399,140 B2 | 7/2016 | Cho et al. |
| 9,724,518 B2 | 8/2017 | Sheldon et al. |
| 9,775,982 B2 | 10/2017 | Grubac et al. |
| 9,814,887 B2 | 11/2017 | Nikolski et al. |
| 2005/0171410 A1 | 8/2005 | Hjelt et al. |
| 2008/0319511 A1 | 12/2008 | Pless |
| 2009/0076343 A1 | 3/2009 | James et al. |
| 2015/0173655 A1 | 6/2015 | Demmer et al. |
| 2015/0305638 A1 | 10/2015 | Zhang et al. |
| 2016/0113586 A1 | 4/2016 | Hemming et al. |
| 2016/0129263 A1 | 11/2016 | Demmer et al. |
| 2017/0056649 A1 | 3/2017 | Kane et al. |
| 2017/0056665 A1 | 3/2017 | Kane et al. |
| 2017/0056666 A1 | 3/2017 | Kane et al. |
| 2017/0274213 A1 | 9/2017 | Ghosh et al. |
| 2018/0085588 A1 | 3/2018 | Splett et al. |
| 2018/0085589 A1 | 3/2018 | Splett et al. |
| 2018/0117337 A1 | 5/2018 | Demmer et al. |
| 2018/0154154 A1 | 6/2018 | Sheldon et al. |
| 2018/0161580 A1 | 6/2018 | Demmer et al. |

OTHER PUBLICATIONS

Splett, et al., U.S. Appl. No. 62/776,034, filed Dec. 6, 2018, 49 pages.
First Office Action for CN Application No. 201980074925.1 dated Jan. 30, 2024, 12 pages.

METHODS AND APPARATUS FOR REDUCING CURRENT DRAIN IN A MEDICAL DEVICE

REFERENCE TO RELATED APPLICATION

This application is a Continuation of U.S. patent application Ser. No. 16/681,278, filed Nov. 12, 2019, which claims the benefit of provisional U.S. Patent Application No. 62/767,009, filed on Nov. 14, 2018, both of which are incorporated herein by reference in their entirety.

TECHNICAL FIELD

This disclosure relates to a medical device and method for reducing the electrical current required for producing a cardiac motion signal.

BACKGROUND

During normal sinus rhythm (NSR), the heart beat is regulated by intrinsic electrical signals produced by the sino-atrial (SA) node located in the right atrial wall. Each atrial depolarization signal produced by the SA node spreads across the atria, causing the depolarization and contraction of the atria, and arrives at the atrioventricular (AV) node. The AV node propagates the depolarization signal to the ventricles through the bundle of His of the ventricular septum and thereafter to the bundle branches and the Purkinje fibers of the right and left ventricles.

Patients with a conduction system abnormality, e.g., poor AV node conduction or poor SA node function, may receive a pacemaker to restore a more normal heart rhythm and AV synchrony. Ventricular pacing may be performed to maintain a ventricular rate in a patient having atrioventricular conduction abnormalities. Dual chamber pacemakers are available which include a transvenous atrial lead carrying electrodes which are placed in the right atrium and a transvenous ventricular lead carrying electrodes that are placed in the right ventricle via the right atrium. The dual chamber pacemaker senses atrial electrical signals and ventricular electrical signals from the respective atrial and ventricular heart chamber electrodes and can provide both atrial pacing and ventricular pacing as needed to promote a normal heart rhythm and AV synchrony. The pacemaker itself is generally implanted in a subcutaneous pocket with the transvenous leads tunneled to the subcutaneous pocket.

Intracardiac pacemakers are available or have been proposed that are implantable within a ventricular chamber of a patient's heart for delivering ventricular pacing pulses. The intracardiac ventricular pacemaker may sense R-wave signals attendant to intrinsic ventricular depolarizations and deliver ventricular pacing pulses in the absence of sensed R-waves. While single chamber ventricular sensing and pacing by an intracardiac ventricular pacemaker may adequately address some heart rhythm conditions, patients having AV block may benefit from atrial-synchronized ventricular pacing in order to promote synchrony between the atrial and ventricular contractions and a more normal heart rhythm.

SUMMARY

The techniques of this disclosure generally relate to a medical device capable of producing a cardiac motion signal that may be used for sensing cardiac mechanical events. Atrial events may be sensed from the cardiac motion signal for triggering ventricular pacing pulses in delivering atrial synchronous ventricular pacing in some examples. The medical device may additionally produce a patient activity signal for determining a patient physical activity metric that may be used for controlling rate responsive ventricular pacing. A medical device operating according to the techniques disclosed herein controls suspending and restarting sampling of a motion sensor signal for producing a cardiac motion signal in a manner that conserves the electrical current required to produce the cardiac motion signal.

In one example, the disclosure provides a medical device including a motion sensing circuit comprising an electrical current source and a multi-axis motion sensor having each axis configured to produce a signal correlated to motion imparted along the respective axis. The motion sensing circuit is configured to produce a cardiac motion signal by sampling a signal produced by an axis of the motion sensor at a sampling frequency by repeatedly applying the current source to the axis for a sample time at time intervals corresponding to the sampling frequency. The motion sensing circuit is further configured to start a blanking period, suspend the sampling of the cardiac motion signal during at least a portion of the blanking period, and restart the sampling of the signal at the sampling frequency before the blanking period has expired. The medical device includes a control circuit configured to receive the cardiac motion signal and detect a cardiac event from the cardiac motion signal. The medical device further includes a pulse generator configured to generate a pacing pulse in response to the control circuit detecting the cardiac event.

In another example, the disclosure provides a method comprising producing a cardiac motion signal by a motion sensing circuit of a medical device by sampling a signal produced by an axis of a multi-axis motion sensor at a sampling frequency by repeatedly applying a current source of the motion sensing circuit to the axis for a sample time at time intervals corresponding to the sampling frequency. The method further includes starting a blanking period, suspending the sampling of the signal during at least a portion of the blanking period, and restarting the sampling of the signal at the sampling frequency before the blanking period has expired. The method may further include detecting a cardiac event from the cardiac motion signal and generating a pacing pulse in response to detecting the cardiac event.

In yet another example, the disclosure provides a non-transitory, computer-readable storage medium comprising a set of instructions which, when executed by a control circuit of a medical device having a motion sensor, cause the medical device to produce a cardiac motion signal by sampling an axis signal produced by an axis of the motion sensor at a sampling frequency by repeatedly applying a current source to the axis for a sample time at time intervals corresponding to the sampling frequency. The instructions further cause the control circuit to start a blanking period, suspend the sampling of the axis signal during at least a portion of the blanking period, and restart the sampling of the axis signal at the sampling frequency before the blanking period has expired. The instructions may further cause the medical device to detect a cardiac event from the cardiac motion signal and generate a pacing pulse in response to detecting the cardiac event.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

In general, this disclosure describes techniques for producing motion signals by a motion sensor of a medical device in a manner that conserves the electrical current required to produce the motion signals. Conserving electrical current required to produce a motion signal, e.g., a motion signal representing cardiac motion, can conserve the medical device power source and extend the useful life of the medical device. In the illustrative examples presented herein, an intracardiac ventricular pacemaker is configured to provide single chamber ventricular pacing and, at least during an atrial synchronous ventricular pacing mode, provide dual chamber (atrial and ventricular) sensing. Atrial systolic events are detected from a cardiac motion signal produced by a motion sensor included in the pacemaker. As described below, the intraventricular cardiac motion signal produced by the pacemaker according to the techniques disclosed herein includes an atrial systolic event signal corresponding to atrial mechanical contraction and the active filling phase of the ventricle, sometimes referred to as the "atrial kick." Atrial systolic event sensing from an intraventricular cardiac motion signal is performed for synchronizing the ventricular pacing pulses delivered by the pacemaker to the atrial rhythm. This atrial synchronized ventricular pacing promotes a more normal heart rhythm in a patient having AV conduction block than asynchronous ventricular pacing that does not track the atrial rhythm.

The intraventricular cardiac motion signal is produced by motion sensing circuitry that includes a motion sensor, such as a multi-axis accelerometer. In various examples, the electrical current that is required to produce the cardiac motion signal is conserved by individually controlling the sampling of each individual axis signal of the multi-axis accelerometer and controlling the time intervals over which each axis signal is produced and sampled. While the illustrative examples disclosed herein relate primarily to producing a cardiac motion signal for detecting atrial mechanical systolic events, it is to be understood that the disclosed techniques for conserving electrical current may be adapted for use in detecting ventricular events by controlling the time intervals over which each axis signal is produced and sampled. More generally, aspects of the techniques disclosed herein may be implemented for conserving current drain of a power source of a medical device for producing a physiological signal from a sensor, such as but not limited to a motion signal produced by an accelerometer.

Figure 1:
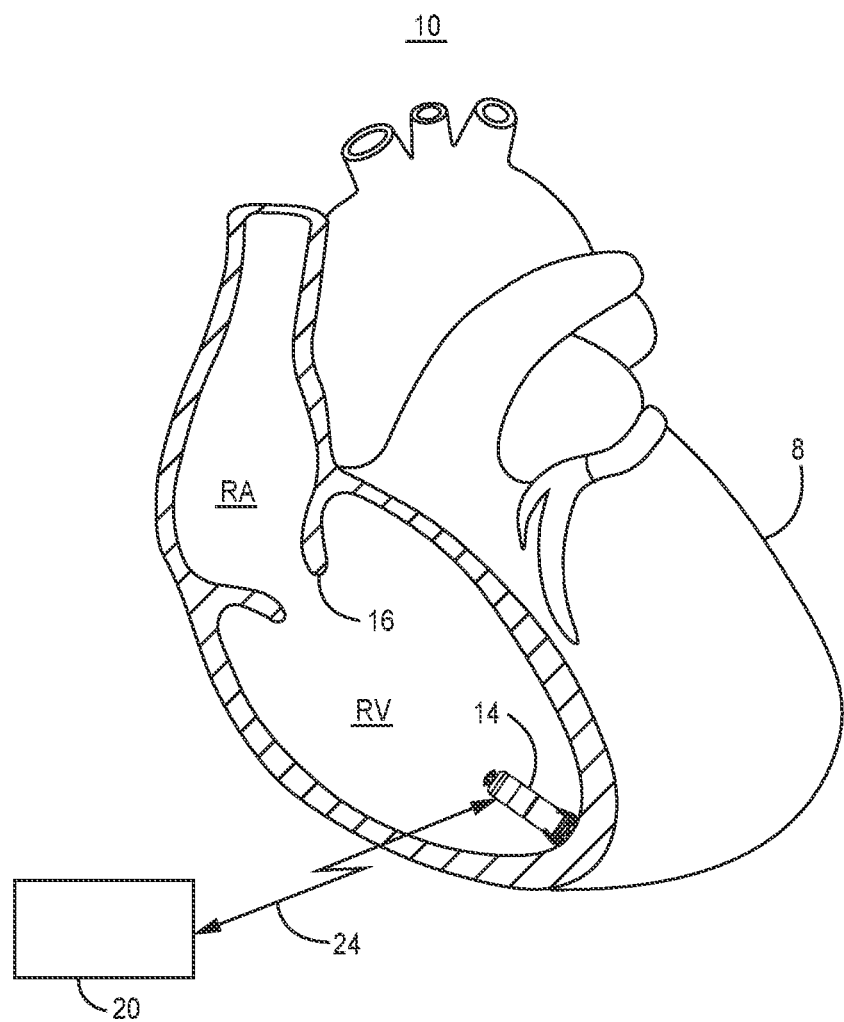
FIG. 1 is a conceptual diagram illustrating an implantable medical device system that may be used to sense cardiac signals and provide ventricular pacing to a patient's heart.

FIG. 1 is a conceptual diagram illustrating an implantable medical device (IMD) system 10 that may be used to sense cardiac signals and provide atrial synchronous ventricular pacing to a patient's heart 8. IMD system 10 includes an intracardiac ventricular pacemaker 14, which may be capable of wireless communication with an external device 20. Pacemaker 14 may be a transcatheter intracardiac pacemaker which is adapted for implantation wholly within a heart chamber, e.g., wholly within the right ventricle (RV) or wholly within the left ventricle (LV) of heart 8 for sensing cardiac signals and delivering ventricular pacing pulses. Pacemaker 14 may be reduced in size compared to subcutaneously implanted pacemakers and may be generally cylindrical in shape to enable transvenous implantation in a heart chamber via a delivery catheter.

In the example shown, pacemaker 14 is positioned along an endocardial wall of the RV, e.g., near the RV apex. The techniques disclosed herein are not limited to the pacemaker location shown in the example of FIG. 1 and other positions within heart 8 are possible. For example, an intracardiac ventricular pacemaker 14 may be positioned in the LV and configured to detect cardiac signals and patient activity and deliver ventricular pacing to the LV using the techniques disclosed herein. Pacemaker 14 may be positioned within the RV or LV to provide respective right ventricular or left ventricular pacing and for sensing atrial signals from within the ventricular chamber for facilitating atrial synchronous ventricular pacing.

Pacemaker 14 may be a leadless pacemaker capable of producing electrical stimulation pulses, e.g., pacing pulses, delivered to heart 8 via one or more electrodes on the outer housing of the pacemaker, referred to herein as "housing based electrodes." Pacemaker 14 is configured to sense a cardiac electrical signal using the housing based electrodes for producing a ventricular electrogram (EGM) signal. The cardiac electrical signals may be sensed using the housing based electrodes that are also used to deliver pacing pulses to the heart 8.

Pacemaker 14 is configured to control the delivery of pacing pulses to the ventricle in a manner that promotes synchrony between atrial systole and ventricular systole, e.g., by maintaining a target atrioventricular (AV) interval between a sensed atrial systolic event and ventricular pacing pulse while operating in an atrial synchronous ventricular pacing mode. Pacemaker 14 senses atrial events from an intraventricular cardiac motion signal produced by a motion sensing circuit included in pacemaker 14, as described below, and controls ventricular pacing pulse delivery to maintain the desired AV interval between sensed atrial systolic mechanical events and subsequent ventricular pacing pulses delivered to cause ventricular depolarization and ventricular systole. The atrial synchronous ventricular pacing mode may be referred to as a "VDD" pacing mode since single chamber ventricular pacing is being delivered with dual chamber sensing and a dual response is provided to sensed events, either a pacing pulse is triggered in response to an atrial sensed event or inhibited in response to an intrinsic ventricular sensed event, e.g., an R-wave.

The atrial synchronous ventricular pacing mode is provided to promote a more normal heart rhythm during periods of AV block. In patients that have AV block (or other conduction abnormalities) intermittently, pacemaker 14 may periodically extend the AV interval or switch to an asynchronous ventricular pacing mode, e.g., VVI or VDI pacing mode, with a low ventricular pacing rate to promote natural AV conduction along the normal conduction pathways of the heart. If AV conduction is determined to be present, the pacemaker 14 may remain in the asynchronous pacing mode at a relatively low lower pacing rate, e.g., 40 to 50 pulses per minute, to promote conduction of atrial depolarizations to the ventricles. If AV block is determined to be present, the pacemaker 14 switches back to the atrial synchronous ventricular pacing mode.

Pacemaker 14 includes a motion sensor, such as an accelerometer, for producing intraventricular motion signals. Controlled sampling of selected axis signals of a multi-axis accelerometer, as described herein, is performed by pacemaker 14 for producing a cardiac motion signal that includes atrial systolic event signals corresponding to the active filling phase of ventricular diastole. Pacemaker 14 may be further configured to produce a patient physical activity signal by sampling at least one selected axis signal of the multi-axis accelerometer. The activity signal is used for detecting patient physical activity level. In some examples, the motion sensor may produce a patient posture signal in addition to the cardiac motion signal and the patient physical activity signal.

Pacemaker 14 may be capable of bidirectional wireless communication with an external device 20 for programming pacing and sensing control parameters. Aspects of external device 20 may generally correspond to the external programming/monitoring unit disclosed in U.S. Pat. No. 5,507, 782 (Kieval, et al.), hereby incorporated herein by reference in its entirety. External device 20 is often referred to as a "programmer" because it is typically used by a physician, technician, nurse, clinician or other qualified user for programming operating parameters in pacemaker 14. External device 20 may be located in a clinic, hospital or other medical facility. External device 20 may alternatively be embodied as a home monitor or a handheld device that may be used in a medical facility, in the patient's home, or another location.

External device 20 establishes a bi-directional wireless communication link 24 with implantable telemetry circuitry included pacemaker 14. Communication link 24 may be established using a radio frequency (RF) link such as BLUETOOTH®, Wi-Fi, Medical Implant Communication Service (MICS) or other communication bandwidth. In some examples, external device 20 may include a programming head that is placed proximate pacemaker 14 to establish and maintain a communication link 24. In other examples external device 20 and pacemaker 14 may be configured to communicate using a distance telemetry algorithm and circuitry that does not require the use of a programming head and does not require user intervention to maintain a wireless communication link. External device 20 may display data and information relating to pacemaker functions to a user for reviewing pacemaker operation and programmed parameters.

A programming head or magnet may be positioned over pacemaker 14 by a user to actuate a switch within pacemaker 14 to initiate a data transmission mode of pacemaker 14 in some examples. Pacemaker 14 may be configured to sample and transmit motion signals, as well as the ventricular EGM signal during the data transmission mode to allow external device 20 to produce a graphical display of a continuous motion signal, e.g., a cardiac motion signal. EGM signals and motion signals produced by pacemaker 14 may be retrieved from pacemaker 14 in real time during a telemetry mode or stored episodes of recorded signals may be retrieved during an interrogation session.

It is contemplated that external device 20 may be in wired or wireless connection to a communications network via a telemetry circuit that includes a transceiver and antenna or via a hardwired communication line for transferring data to a centralized database or computer to allow remote management of the patient. Remote patient management systems including a remote patient database may be configured to utilize the presently disclosed techniques to enable a clinician to review EGM signals, motion signals, and marker channel data and authorize programming of sensing and therapy control parameters in pacemaker 14, e.g., after viewing a visual representation of EGM, motion signals and marker channel data (e.g., as show in FIG. 8).

Figure 2:
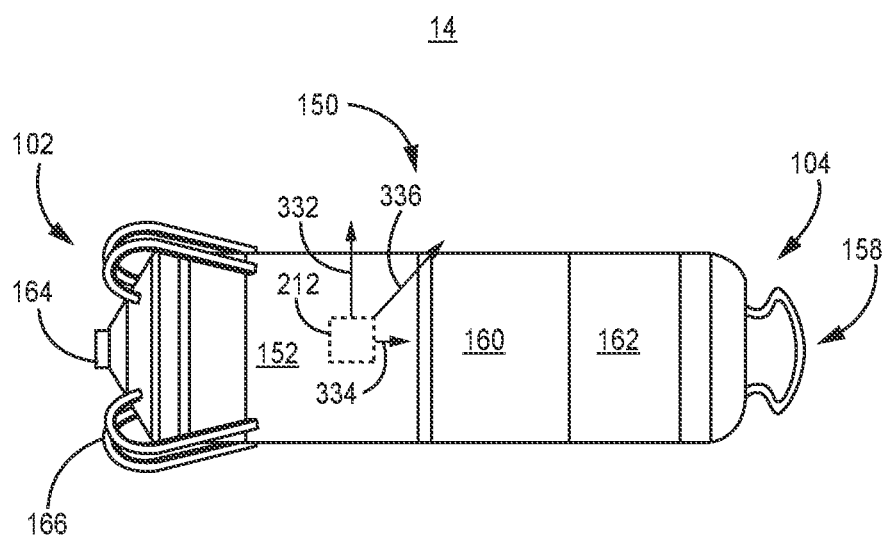
FIG. 2 is a conceptual diagram of the intracardiac ventricular pacemaker shown in FIG. 1.

FIG. 2 is a conceptual diagram of the intracardiac pacemaker 14 shown in FIG. 1. Pacemaker 14 includes leadless electrodes 162 and 164 spaced apart on the housing 150 of pacemaker 14 for sensing cardiac electrical signals and delivering pacing pulses. Electrode 164 is shown as a tip electrode extending from a distal end 102 of pacemaker 14, and electrode 162 is shown as a ring electrode along a mid-portion of the lateral wall of housing 150, for example adjacent proximal end 104. Electrode 162 may circumscribe a portion of the lateral sidewall of housing 152 that extends from distal end 102 to proximal end 104. Distal end 102 is referred to as "distal" in that it is expected to be the leading end as pacemaker 14 is advanced through a delivery tool, such as a catheter, and placed against a targeted pacing site.

Electrodes 162 and 164 form an anode and cathode pair for bipolar cardiac pacing and cardiac electrical signal sensing. In other examples, pacemaker 14 may include two or more ring electrodes, two tip electrodes, and/or other types of electrodes exposed along pacemaker housing 150 for delivering electrical stimulation to heart 8 and sensing cardiac electrical signals. Electrodes 162 and 164 may be positioned at locations along pacemaker 14 other than the locations shown. Electrodes 162 and 164 may be, without limitation, titanium, platinum, iridium or alloys thereof and may include a low polarizing coating, such as titanium nitride, iridium oxide, ruthenium oxide, platinum black among others.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. Electrode 164 may serve as a cathode electrode and be coupled to internal circuitry, e.g., a pacing pulse generator and cardiac electrical signal sensing circuitry, enclosed by housing 150 via an electrical feedthrough crossing housing 150. Electrode 162 may be formed as a conductive portion of housing 150 defining a ring electrode that is electrically isolated from the other portions of the housing 150 as generally shown in FIG. 2. In other examples, the entire periphery of the housing 150 may function as an electrode that is electrically isolated from tip electrode 164, instead of providing a localized ring electrode such as anode electrode 162. Electrode 162 defined by an electrically conductive portion of housing 150 serves as a return anode during pacing and sensing.

The housing 150 includes a control electronics subassembly 152, which houses the electronics for sensing cardiac signals, producing pacing pulses and controlling therapy delivery and other functions of pacemaker 14 as described below in conjunction with FIG. 3. Control electronics subassembly 152 includes a motion sensing circuit 212 having a motion sensor that may be implemented as an accelerometer, enclosed within housing 150 in some examples. The motion sensor may be a multi-axis motion sensor, e.g., a three-dimensional accelerometer, which produces a signal from each axis correlated to motion imparted along the respective axis. In the example shown, a motion sensor included in motion sensing circuit 212 has three orthogonal axes 332, 334 and 336. One axis 334 may be aligned with a longitudinal axis of the elongated housing 150. The other two axes 332 and 336 may be radial axes that extend orthogonally to each other and the longitudinal axis 334. Motion sensing circuit 212 produces motion signals that are passed to control circuitry included in control electronics subassembly 152 for signal processing and analysis for sensing atrial systolic events and detecting patient physical activity as described below. The techniques disclosed herein conserve the electrical current required by motion sensing circuit 212 for producing a cardiac motion signal using one, two or all three axis signals.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 14 may include a set of fixation tines 166 to secure pacemaker 14 to patient tissue, e.g., by actively engaging with the ventricular endocardium and/or interacting with the ventricular trabeculae. Fixation tines 166 are configured to anchor pacemaker 14 to position electrode 164 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may include a set of fixation tines as disclosed in commonly-assigned U.S. Pat. No. 9,775,982 (Grubac, et al.), hereby incorporated herein by reference in its entirety.

Pacemaker 14 may optionally include a delivery tool interface 158. Delivery tool interface 158 may be located at the proximal end 104 of pacemaker 14 and is configured to connect to a delivery device, such as a catheter, used to position pacemaker 14 at an implant location during an implantation procedure, for example within a ventricular heart chamber.

Figure 3:
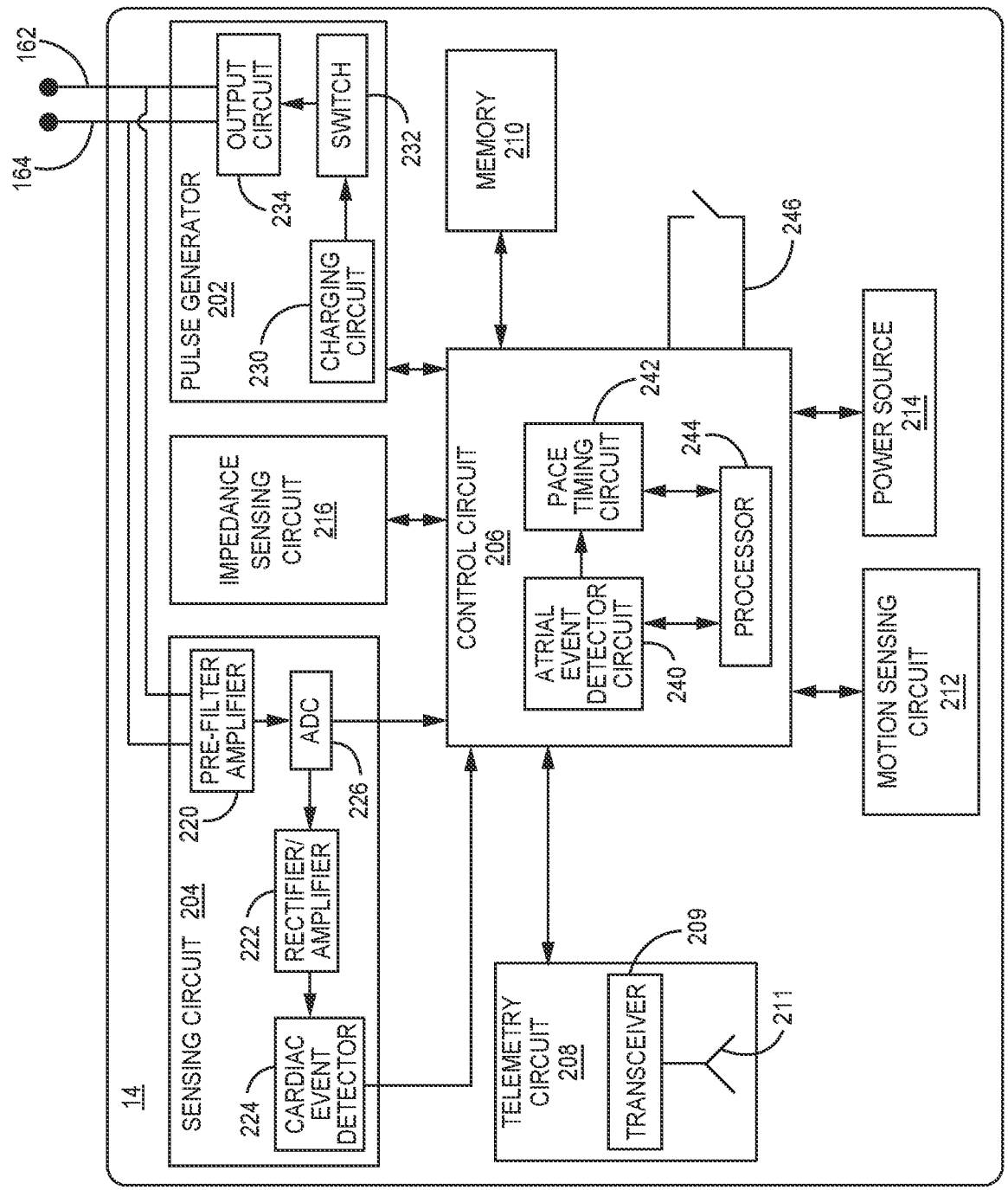
FIG. 3 is a schematic diagram of an example configuration of the pacemaker shown in FIG. 1.

FIG. 3 is a schematic diagram of an example configuration of pacemaker 14 shown in FIG. 1. Pacemaker 14 includes a pulse generator 202, a cardiac electrical signal sensing circuit 204, a control circuit 206, memory 210, telemetry circuit 208, motion sensing circuit 212 and a power source 214. The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Motion sensing circuit 212 includes a motion sensor implemented as an accelerometer in the examples described herein. Motion sensing circuit 212 is not limited to being an accelerometer, however, and other motion sensors may be utilized successfully in pacemaker 14 for detecting cardiac motion signals according to the techniques described herein. Examples of motion sensors that may be implemented in motion sensing circuit 212 include piezoelectric sensors and micro-electrical mechanical system (MEMS) devices.

Motion sensing circuit 212 may include a single axis, one-dimensional sensor or a multi-axis sensor, e.g., a two-dimensional or three-dimensional sensor with each axis providing a signal that may be used individually or in combination with one or more other axis signals, for producing a cardiac motion signal for detecting cardiac mechanical events. At least one axis signal may be used for producing a patient physical activity signal, and in some examples a patient posture signal may be produced from an accelerometer axis signal or signals.

Each axis of the accelerometer included in motion sensing circuit 212 produces an electrical signal correlated to motion or vibration imparted on accelerometer (and pacemaker 14) along the respective axis, e.g., when subjected to flowing blood, cardiac motion and patient body motion due to physical activity such as exercise and activities of daily living or other motion imposed on the patient such as riding in a car. Each axis of a single or multi-dimensional accelerometer may be defined by a piezoelectric element, MEMS device or other sensor element capable of producing an electrical signal in response to changes in acceleration imparted on the sensor element, e.g., by converting the acceleration to a force or displacement that is converted to the electrical signal. In a multi-dimensional accelerometer, the sensor elements may be arranged orthogonally with each sensor element axis orthogonal relative to the other sensor element axes. Orthogonal arrangement of the elements of a multi-axis accelerometer, however, is not necessarily required.

One example of an accelerometer for use in implantable medical devices is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers that may be implemented in pacemaker 14 and used for producing a cardiac motion signal using the presently disclosed techniques are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to motion imparted on pacemaker 14 due to ventricular and atrial events, patient physical activity and posture. Motion sensing circuit 212 may include filters, amplifiers, rectifiers, analog-to-digital converters (ADCs) and/or other components for producing a motion signal passed to control circuit 206. Circuitry included in motion sensing circuit 212 is described below in conjunction with FIG. 6.

Cardiac electrical signal sensing circuit 204 is configured to receive a cardiac electrical signal via electrodes 162 and 164 by a pre-filter and amplifier circuit 220. Pre-filter and amplifier circuit may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to ADC 226. ADC 226 may pass a multi-bit, digital electrogram (EGM) signal to control circuit 206 for use in detecting cardiac events and determining a patient's heart rhythm. The digital signal from ADC 226 may be passed to rectifier and amplifier circuit 222, which may include a rectifier, bandpass filter, and amplifier for passing the filtered and rectified cardiac electrical signal to cardiac event detector 224.

Cardiac event detector 224 may include a sense amplifier, comparator or other detection circuitry that compares the incoming rectified, cardiac electrical signal to an R-wave detection threshold amplitude, which may be an auto-adjusting threshold. When the incoming signal crosses the R-wave detection threshold, the cardiac event detector 224 produces an R-wave sensed event signal that is passed to control circuit 206. R-wave sensed event signals passed from cardiac event detector 224 to control circuit 206 may be used for scheduling ventricular pacing pulses and determining ventricular rate intervals or RR intervals (between two consecutively received R-wave sensed event signals).

Control circuit 206 may receive R-wave sensed event signals and/or digital cardiac electrical signals from sensing circuit 204 for use in detecting and confirming cardiac events and controlling ventricular pacing. For example, R-wave sensed event signals may be passed to pace timing circuit 242 for inhibiting scheduled ventricular pacing pulses during atrial synchronous ventricular pacing or scheduling ventricular pacing pulses when pacemaker 14 is operating in a non-atrial tracking (asynchronous) ventricular pacing mode.

Control circuit 206 includes an atrial event detector circuit 240, pace timing circuit 242, and processor 244. Atrial event detector circuit 240 is configured to detect atrial systolic mechanical events from a cardiac motion signal received from motion sensing circuit 212. In some examples, one or more ventricular mechanical events may be detected from the cardiac motion sensor signal in a given cardiac cycle to facilitate positive detection of the atrial systolic event from the cardiac motion signal during the ventricular cycle or in establishing atrial systolic event sensing control parameters.

R-wave sensed event signals may be passed to atrial event detector circuit 240 for use in setting post-ventricular atrial blanking (PVAB) periods and/or time windows used by control circuit 206 in sensing atrial systolic events from the cardiac motion signal. Atrial event detector circuit 240 receives the cardiac motion signal from motion sensing circuit 212. Atrial event detector circuit 240 may start a PVAB period in response to a ventricular electrical event, e.g., an R-wave sensed event signal from sensing circuit 204 or generation of a ventricular pacing pulse by pulse generator 202. The PVAB period may correspond to a time period after the ventricular electrical event during which ventricular mechanical events, e.g., corresponding to ventricular contraction, are expected to occur. Cardiac motion signal peaks that occur during the PVAB period are not sensed as atrial events to avoid falsely sensing a ventricular motion signal event as the atrial systolic event.

Atrial event detector circuit 240 determines if the motion sensor signal satisfies atrial systolic event detection criteria outside of the PVAB period. Atrial event detector circuit 240 may set time windows corresponding to the passive ventricular filling phase and the active ventricular filling phase based on the timing of a preceding ventricular electrical event, either an R-wave sensed event signal or a ventricular pacing pulse. As described below, two different atrial event sensing threshold amplitude values may be established for applying during the passive filling phase window and after the passive filling phase window. The earliest crossing of the atrial event sensing threshold amplitude by the cardiac motion signal after the PVAB period may be detected as the atrial systolic event.

Atrial event detector circuit 240 passes an atrial event detection signal to processor 244 and/or pace timing circuit 242 in response to detecting an atrial systolic event. Processor 244 may include one or more clocks for generating clock signals that are used by pace timing circuit 242 to time out an AV pacing interval that is started upon receipt of an atrial event detection signal from atrial event detector circuit 240. Pace timing circuit 242 may include one or more pacing escape interval timers or counters that are used to time out the AV pacing interval, which may be a programmable interval stored in memory 210 and retrieved by processor 244 for use in setting the AV pacing interval used by pace timing circuit 242.

Pace timing circuit 242 (or processor 244) may additionally receive R-wave sensed event signals from cardiac event detector 224 for use in controlling the timing of pacing pulses delivered by pulse generator 202. Pace timing circuit 242 may include a lower pacing rate interval timer for controlling a lower ventricular pacing rate. For example, if an atrial systolic event is not detected from the motion sensor signal, a ventricular pacing pulse may be delivered by pulse generator 202 upon expiration of the lower rate pacing interval to prevent ventricular asystole and maintain a minimum ventricular rate. In order to avoid abrupt changes in ventricular rate, control circuit 206 may be configured to adjust the lower rate pacing interval to a rate smoothing interval. The rate smoothing interval may be based on one or more preceding ventricular event intervals. For example, a ventricular pacing pulse delivered in the absence of a sensed atrial event during the atrial synchronous ventricular pacing mode may be delivered at a rate smoothing interval that is within a predetermined interval of preceding Vpace-to-Vpace intervals or a median RR interval, e.g., not more than 100 to 150 ms greater than the actual preceding ventricular rate interval(s).

At times, control circuit 206 may control pulse generator 202 in an asynchronous ventricular pacing mode, e.g., when ventricular rate support is needed during patient activity or when AV conduction is intact. During the asynchronous ventricular pacing mode, pace timing circuit 242 may set a VV pacing interval to a lower pacing rate interval corresponding to a programmed minimum base rate, which may be 60 pulses per minute or less, e.g., 40 pulses per minute. Pacemaker 14 may adjust the VV pacing interval from the minimum lower rate interval to a higher, temporary lower rate interval set based on a patient physical activity metric to provide rate responsive ventricular pacing that supports the metabolic demand of the patient. The activity metric may be determined by control circuit 206 from a patient physical activity signal produced by motion sensing circuit 212. Control circuit 206 may remain in the asynchronous pacing mode as long as ventricular rate support is needed based on a patient activity signal received from motion sensing circuit 212 or AV conduction is intact. If AV block is detected and the patient returns to a resting activity level, however, control circuit 206 may switch back to the atrial synchronous ventricular pacing mode to promote AV synchrony.

The patient activity metric may be determined at a desired frequency, e.g., every two seconds, for use in determining a sensor-indicated pacing rate (SIR) that meets the metabolic requirements of the patient based on physical activity. The SIR may vary between the programmed minimum lower rate during periods of rest (minimal activity metric) and a maximum upper pacing rate during periods of maximum exertion. The SIR may be controlled according to a SIR transfer function, which may include different rates of change of the SIR over different ranges of the patient activity metric.

In some examples, the activity metric is determined as an activity count. In these instances, control circuit 206 includes a counter to track the activity count as the number of times the activity signal from motion sensing circuit 212 crosses a threshold amplitude during an activity count interval, for example a 2-second interval. The count at the end of each activity count interval is correlated to patient body motion during the activity count interval and is therefore correlated to patient metabolic demand. Example methods for obtaining an activity count over an n-second interval are generally disclosed in U.S. Pat. No. 5,720,769 (van Oort), incorporated herein by reference in its entirety.

In other examples, an activity metric may be obtained from the patient physical activity signal by integrating or summing activity signal sample points over an activity count interval, e.g., a two-second interval though longer or shorter intervals of time may be used for determining an activity metric. The activity metric may be converted to a target heart rate to meet the patient's metabolic demand. The target heart rate may be converted to a SIR based on a SIR transfer function that includes a lower rate set point and an activities of daily living (ADL) range. As long as the activity metric is at or below the lower rate set point, the SIR remains at the programmed minimum lower rate.

As the activity count increases above the lower rate set point, the SIR may be determined according to the SIR transfer function slope or profile up to the ADL range. As long as the patient activity metric (and resulting target heart rate) remains between a lower and upper boundary of the ADL range, the SIR is set to an ADL rate, which is greater than the programmed minimum lower rate and is expected to provide adequate pacing support to the patient during normal daily activities, such as moving about the home, driving a car, light tasks, etc.

If the activity metric and resultant target heart rate rises to be greater than the ADL range, the SIR is increased according to a slope or profile of the SIR transfer function over the range from the upper boundary of the ADL range to reach the target heart rate, up to the maximum upper rate set point. The SIR is set to the maximum upper pacing rate for all activity metrics greater than the maximum upper rate set point. Each of the lower rate set point, the ADL range and the maximum upper rate set point may be tailored to a patient's particular needs based on activity metric history. In order to avoid abrupt changes in pacing rate, the target heart rate may be determined from the patient activity metric, and the SIR may be determined from the target rate according to the transfer function that controls how quickly the SIR accelerates or decelerates up to or down to the target rate as patient activity increases or decreases, respectively. Examples of methods for establishing a SIR transfer function applied to patient activity metrics determined from an intraventricular motion signal are generally disclosed in U.S. Pat. No. 9,724,518 (Sheldon, et al.), incorporated herein by reference in its entirety.

Control circuit 206 may pass cardiac electrical event signals to motion sensing circuit 212 to indicate the timing of a ventricular pacing pulse or an R-wave sensed event signal. As described below, motion sensing circuit 212 may set a PVAB period in response to the cardiac electrical event signal. Motion sensing circuit 212 may withhold electrical current from one or more axes of the accelerometer during the PVAB period to reduce the electrical current required to produce the cardiac motion signal. The cardiac motion sensing circuit 212 may apply electrical current at a sampling rate to the accelerometer axis or axes selected for producing the cardiac motion signal beginning just prior to the expiration of the PVAB period to produce the cardiac motion signal that is passed to atrial event detector circuit 240 for atrial event detection after the expiration of the PVAB period. By withholding electrical current from one or more axes of the accelerometer during at least a portion of the PVAB period, electrical current and power source 214 are conserved, compared to producing the cardiac motion signal throughout the cardiac cycle.

Processor 244 may retrieve programmable pacing control parameters, such as pacing pulse amplitude and pacing pulse width, which are passed to pulse generator 202 for controlling pacing pulse delivery from memory 210. In addition to providing control signals to pace timing circuit 242 and pulse generator 202 for controlling pacing pulse delivery, processor 244 may provide sensing control signals to cardiac electrical signal sensing circuit 204 (e.g., R-wave sensing threshold, sensitivity, and/or various blanking and refractory intervals applied by cardiac event detector 224 to the cardiac electrical signal), motion sensing circuit 212 and atrial event detector circuit 240 for sensing atrial events from the cardiac motion signal as described below.

Pulse generator 202 generates electrical pacing pulses that are delivered to the RV of the patient's heart via cathode electrode 164 and return anode electrode 162. Pulse generator 202 may include charging circuit 230, switching circuit 232 and an output circuit 234. Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of a pacing interval, e.g., an AV pacing interval, a VV rate smoothing interval, a SIR interval, or VV lower rate interval, and kept closed for a programmed pacing pulse width to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration. Examples of pacing circuitry generally disclosed in U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 206 for generating and delivering a pacing pulse.

Memory 210 may include computer-readable instructions that, when executed by control circuit 206, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media. Memory 210 may store timing intervals and other data used by control circuit 206 to control the delivery of pacing pulses by pulse generator 202 according to the techniques disclosed herein.

Power source 214 may correspond to battery subassembly 160 shown in FIG. 2 and provides power to each of the other circuits and components of pacemaker 14 as required. Power source 214 may include one or more energy storage devices, such as one or more rechargeable or non-rechargeable batteries. The connections between power source 214 and other pacemaker circuits and components are not shown in FIG. 3 for the sake of clarity but are to be understood from the general block diagram of FIG. 3. For example power source 214 may provide power to charging circuit 230 for charging a holding capacitor to a pacing voltage amplitude, current to switch 232 and other circuitry included in pulse generator 202 as needed to generate and deliver pacing pulses. Power source 214 also provides power to telemetry circuit 208, motion sensing circuit 212, and cardiac electrical signal sensing circuit 204 as needed as well as memory 210.

Telemetry circuit 208 includes a transceiver 209 and antenna 211 for transferring and receiving data, e.g., via a radio frequency (RF) communication link. Telemetry circuit 208 may be capable of bi-directional communication with external device 20 (FIG. 1) as described above. Motion sensor signals and cardiac electrical signals, and/or data derived therefrom may be transmitted by telemetry circuit 208 to external device 20. Programmable control parameters and programming commands for performing atrial event detection and ventricular pacing control according to the techniques disclosed herein may be received by telemetry circuit 208 and stored in memory 210 for access by control circuit 206.

Pacemaker 14 may include a reed switch 246 or other actuatable switch for enabling a telemetry mode for transmitting signals to a programmer or other external device 20 (FIG. 1) via telemetry circuit 208. A magnet or programming head positioned externally over pacemaker 14 actuates the reed switch 246. In response to detecting the telemetry mode, e.g., based on the closure of the reed switch 246, control circuit 206 may control cardiac electrical signal sensing circuit 204, motion sensing circuit 212, and telemetry circuit 208 to cooperatively produce and transmit a ventricular EGM signal, the cardiac motion signal, and marker channel signals indicating the timing of sensed cardiac events and ventricular pacing pulses. The signals may be transmitted in real time to allow a user or clinician to view the relative timing of sensed cardiac events, e.g., R-waves and atrial systolic events, and delivered ventricular pacing pulses.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, atrial systolic event detection from the motion sensor signal and ventricular pacing control operations performed by pacemaker 14 may be implemented in control circuit 206 executing instructions stored in memory 210 and relying on input from cardiac electrical signal sensing circuit 204 and motion sensing circuit 212.

The operation of circuitry included in pacemaker 14 as disclosed herein should not be construed as reflective of a specific form of hardware, firmware and software necessary to practice the techniques described. It is believed that the particular form of software, hardware and/or firmware will be determined primarily by the particular system architecture employed in the pacemaker 14 and by the particular sensing and therapy delivery circuitry employed by the pacemaker 14. Providing software, hardware, and/or firmware to accomplish the described functionality in the context of any modern pacemaker, given the disclosure herein, is within the abilities of one of skill in the art.

Figure 4:
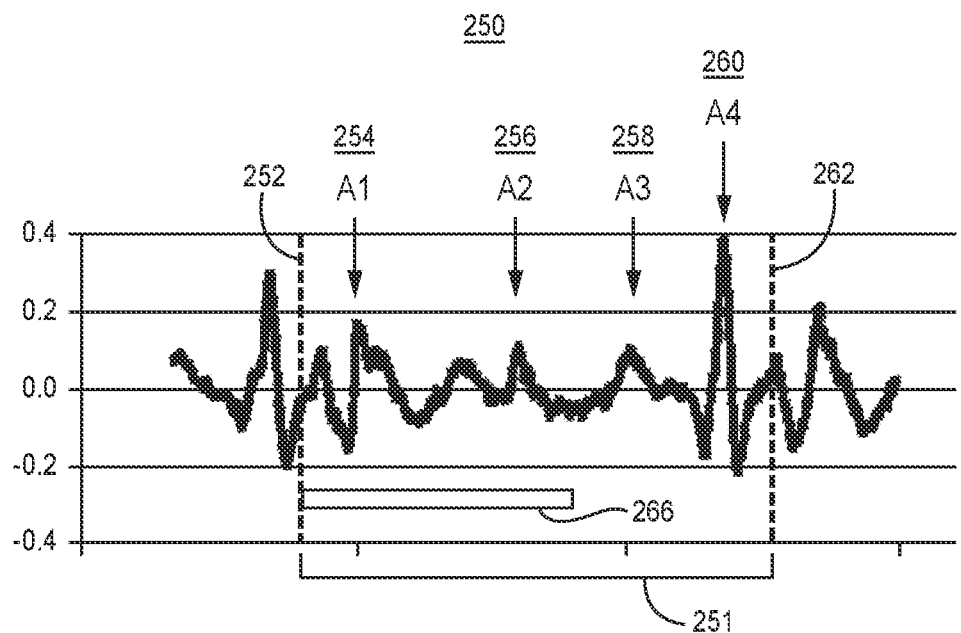
FIG. 4 is an example of a cardiac motion signal that may be produced by the pacemaker of FIG. 1 over a cardiac cycle.

FIG. 4 is an example of a cardiac motion signal 250 that may be produced by motion sensing circuit 212 over a cardiac cycle. Vertical dashed lines 252 and 262 denote the timing of two consecutive ventricular events (an intrinsic ventricular depolarization or a ventricular pace), marking the respective beginning and end of the ventricular cycle 251. The cardiac motion signal 250 includes an A1 event 254, an A2 event 256, an A3 event 258 and an A4 event 260. The A1 event 254 is an acceleration signal that occurs during ventricular contraction and marks the approximate onset of ventricular mechanical systole. The A1 event is also referred to herein as a "ventricular contraction event." The A2 event 256 is an acceleration signal that may occur during closure of the aortic and pulmonic valves and marks the approximate offset or end of ventricular mechanical systole. The A2 event may also mark the beginning of ventricular diastole and is generally an indication of the isovolumic relaxation phase of the ventricles that occurs with aortic and pulmonic valve closure. The A3 event 258 is an acceleration signal that occurs during passive ventricular filling and marks ventricular mechanical diastole. The A3 event is also referred to herein as the "ventricular passive filling event."

The A4 event 260 is an acceleration signal that occurs during atrial contraction and active ventricular filling and marks atrial mechanical systole. The A4 event 260 may also be referred to herein as the "atrial systolic event" or merely the "atrial event," and is the atrial systolic event that is detected from cardiac motion signal 250 by atrial event detector circuit 240 for controlling pace timing circuit 242 to trigger ventricular pacing pulse delivery by starting an AV pacing interval in response to detecting the A4 event 260. A post ventricular atrial blanking (PVAB) period 266 may be set by control circuit 206 in response to a delivered ventricular pacing pulse or sensed R-wave. During the PVAB period, atrial event detection circuit 240 does not detect A4 events from the cardiac motion signal 250 to avoid oversensing the ventricular A1 and A2 events as A4 events.

Figure 5:
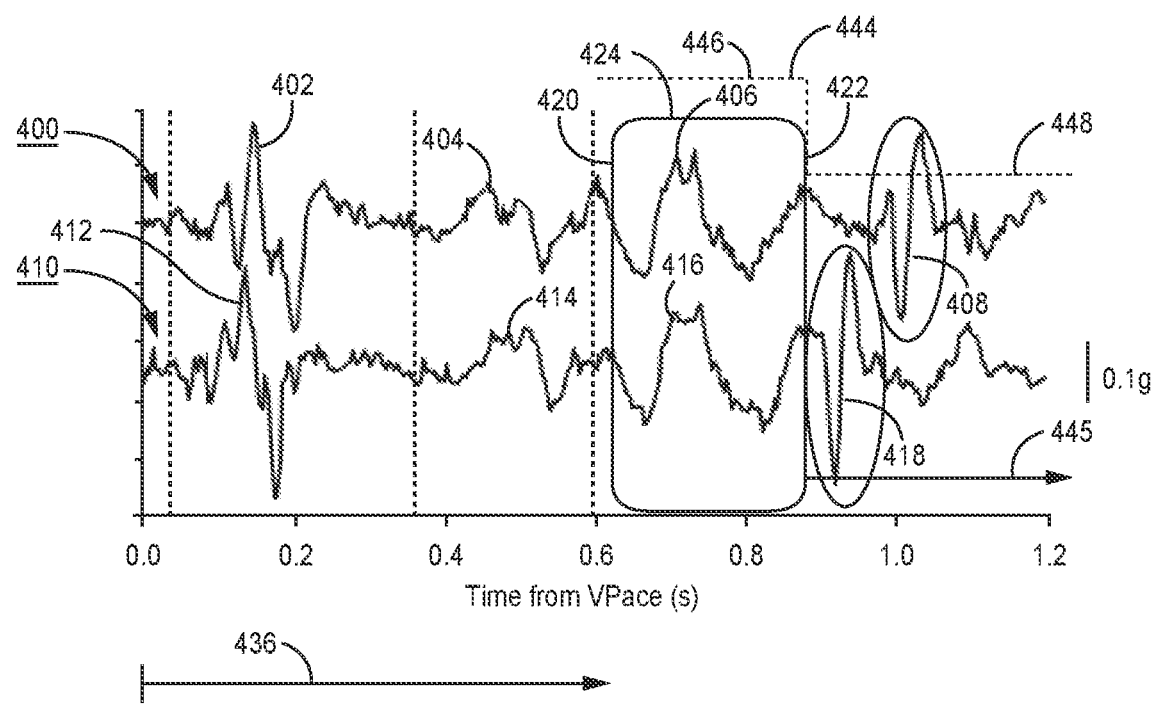
FIG. 5 depicts example cardiac motion signals acquired over two different cardiac cycles.

FIG. 5 depicts example cardiac motion signals 400 and 410 acquired over two different cardiac cycles. A ventricular pacing pulse is delivered at time 0.0 seconds for both cardiac cycles. The top cardiac motion signal 400 is received over one cardiac cycle and the bottom cardiac motion signal 410 is received over a different cardiac cycle. The two signals 400 and 410 are aligned in time at 0.0 seconds, the time of the ventricular pacing pulse delivery. While cardiac motion signals 400 and 410 and cardiac motion signal 250 of FIG. 4 are shown as raw accelerometer signals, it is recognized that control circuit 206 may receive a filtered, amplified and rectified signal from motion sensing circuit 212 for detecting atrial events by atrial event detector circuit 240.

The A1 events 402 and 412 of the respective cardiac motion signals 400 and 410, which occur during ventricular contraction, are observed to be well-aligned in time following the ventricular pacing pulse at time 0.0 seconds. Similarly, the A2 events 404 and 414 and the A3 events 406 and 416 (occurring during passive ventricular filling) are well-aligned in time. Since the A1, A2 and A3 events are ventricular events, occurring during ventricular contraction, ventricular isovolumic relaxation, and passive ventricular filling, respectively, these events are expected to occur at relatively consistent time intervals following a ventricular electrical event, the ventricular pacing pulse in this example, and relative to each other. The time relationship of the A1, A2 and A3 events may be different following a ventricular pacing pulse compared to following a sensed intrinsic R-wave and may change with heart rate; however, during a stable paced or intrinsic ventricular rhythm, the relative timing of A1, A2 and A3 events to each other and the immediately preceding ventricular electrical event is expected to be consistent.

The A4 events 408 and 418 of the cardiac motion signals 400 and 410 respectively are not aligned in time. The A4 event occurs due to atrial systole and as such the time interval to the A4 event following the immediately preceding ventricular electrical event (sensed R-wave or ventricular pacing pulse) and the preceding A1 through A3 events may vary between cardiac cycles due to changes in the atrial rate.

The consistency of the timing of the A1 through A3 events relative to each other and the immediately preceding ventricular electrical event may be used for determining PVAB period 436 and increasing confidence in reliably detecting A4 events 408 and 418. The atrial systolic event is not detected during the PVAB period 436 which extends from the ventricular electrical event (at time 0.0) to an estimated onset of ventricular diastole, for example. An A3 window 424 may be set having a starting time 420 corresponding to the end of the PVAB period 436 and extend to an ending time 422. The PVAB period 436 may be 600 ms, as an example, and the A3 window 424 may extend 200 ms after PVAB period 436.

As seen by the lower cardiac motion signal 410, the A4 event 418 may occur earlier after the A3 window 424 due to changes in atrial rate. In some instances, as the atrial rate increases, the A4 event 418 may occur within the A3 window 424. When this occurs, the A3 event 416 and the A4 event 418 may fuse as passive and active ventricular filling occur together. The fused A3/A4 event may have a high amplitude, even greater than the amplitude of either the A3 event 416 or the A4 event 418 when they occur separately. In order to promote A4 sensing even when the atrial rate is increasing, the PVAB period 436 may end prior to the A3 event 406, 416 because as the atrial rate increases, the A4 event 408, 418 may occur relatively earlier after the ventricular pacing pulse or R-wave and even fuse with the A3 event 406, 416.

To avoid falsely oversensing of the A3 event as an A4 event during the A3 window 424, after PVAB period 436, A4 events 408 and 418 may be detected based on a multi-level A4 detection threshold 444. The A4 detection threshold 444 includes a first, higher A4 threshold amplitude 446 established for detecting an early A4 event that is fused with the A3 event during the A3 window 424. A second, lower A4 threshold amplitude 448 may be established for detecting relatively later A4 events, after the ending time 422 of the A3 window 424. An A4 window 445 may extend from the end of the A3 window 424 until an atrial event is sensed or a ventricular event occurs, whichever occurs first. The earliest crossing of the A4 detection threshold 444 by the cardiac motion signal after the starting time 420 of the A3 window (after the expiration of PVAB period 436) may be sensed as the atrial systolic event. Various examples of an intracardiac pacemaker configured to detect atrial systolic events from a motion sensor signal for delivering atrial synchronous ventricular pacing are disclosed in commonly-assigned U.S. Publication No. 2018/0085589 (Splett et al.), U.S. Publication No. 2018/0085588 (Splett, et al.), U.S. Publication No. 2018/0117337 (Demmer, et al.), U.S. Publication No. 2018/0154154 (Sheldon, et al.), and U.S. Publication No. 2018/0161580 (Demmer, et al.), all of which are incorporated herein by reference in their entirety. The techniques disclosed herein for reducing electrical current required to produce a cardiac motion signal may be implemented in any of the examples presented in the foregoing incorporated references.

Figure 6:
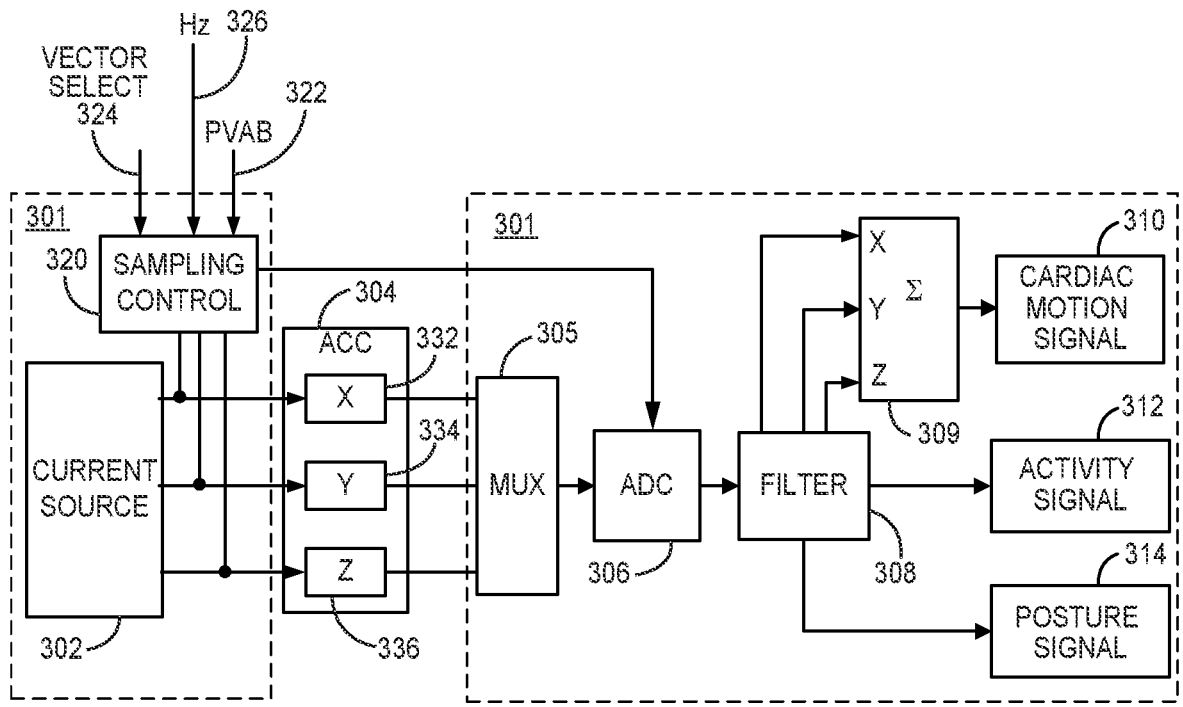
FIG. 6 is a conceptual diagram of the motion sensing circuit shown in FIG. 3.

FIG. 6 is a conceptual diagram of motion sensing circuit 212 included in pacemaker 14 according to one example. Motion sensing circuit 212 includes accelerometer 304 and an electronic interface circuit 301 that includes a current source 302, sampling control circuit 320, multiplexor 305, ADC 306, and filter 308 for producing a cardiac motion signal 310, patient physical activity signal 312 (also referred to herein as "activity signal"), and optionally a patient posture signal 314. Accelerometer 304 is shown to include three axes, X-axis 332, Y-axis 334, and Z-axis 336. As described above in conjunction with FIG. 2, the Y-axis 334 may be aligned with the longitudinal axis of pacemaker housing 150, and the X-axis 332 and Z-axis 336 may be orthogonal to one another and to the Y-axis 334, each extending in radial directions relative to the longitudinal axis of pacemaker housing 150. Other orthogonal or non-orthogonal arrangements of two or more axes of a multi-axis accelerometer may be used with the techniques disclosed herein.

In one example, each axis 332, 334 and 336 of accelerometer 304 may be defined by a capacitive accelerometer element with each element coupled to the electronic interface circuit 301. Each capacitive accelerometer element defining a given axis may be implemented as a MEMS device, for example, and include two parallel fixed capacitor plates and a spring mounted capacitor plate movable (and parallel) between the fixed parallel plates. The orientation of multiple capacitive plate pairs defining each axis provides sensitivity to acceleration along the multiple axes. For example, each capacitive accelerometer element may be oriented orthogonally to the orientation of the other two capacitive elements such that each axis is responsive to motion along a vector aligned with a given axis in a local x-, y-, z-coordinate system. Each capacitive accelerometer element is responsive to both static (e.g., gravitational) and dynamic accelerations. The distance between the movable plate and each of the fixed plates changes due to the force of gravity and motion imposed along a vector corresponding to the accelerometer axis. As the displacement of the moveable plate changes (e.g., as it moves closer to one fixed plate and moves away from the other fixed plate), the capacitance between each pair of parallel plates changes in proportion to the change in displacement of the movable plate.

The current source 302 applies current across capacitive accelerometer elements of each axis that is selected for producing the cardiac motion signal 310, patient activity signal 312, and optionally posture signal 314 under the control of sampling control 320. Current source 302 is powered by pacemaker power source 214 for applying the electrical current signal to each capacitive accelerometer element of the multi-axis accelerometer 304. The electronic interface circuit 301 receives a resulting voltage signal from each axis 332, 334 and 336 that is being sampled. The resulting voltage signal varies with the varying displacement of the movable plate and resultant varying capacitance of the sampled accelerometer axis.

The electronic interface circuit 301 converts the voltage developed in response to the current signal injected by current source 302 and the varying capacitance of each of the sampled axes 332, 334, and 336 to an output signal, which may be the cardiac motion signal 310, activity signal 312 and/or posture signal 314. A signal from a given axis 332, 334 or 336 is "sampled" when sampling control circuit 320 couples the current source 302 to the respective axis to produce the resultant voltage signal that is passed to multiplexer 305.

Sampling control circuit 320 controls when current source 302 is coupled to each axis 332, 334 and 336, i.e., when current source 302 is coupled to each capacitive accelerometer element of each respective axis 332, 334 and 336, according to a sampling rate used to produce the cardiac motion signal 310, activity signal 312, and optionally posture signal 314. Sampling control circuit 320 may include registers, switches and other control circuitry for controlling when current source 302 is coupled to each axis of accelerometer 304 according to the selected sampling rate and sampling time periods for each axis individually.

Sampling control circuit 320 receives control signals from control circuit 206 for use in controlling when the current source 302 is coupled to each axis of accelerometer 304 to produce an axis signal. Control signals may include a PVAB signal 322, a vector selection signal 324 and a sampling frequency selection signal 326. The vector selection signal 324 is used to select which of the accelerometer axes are sampled for producing each of the cardiac motion signal 310, activity signal 312 and posture signal 314. In some examples, a default axis may be automatically selected for producing activity signal 312. For example, the default axis for producing a patient physical activity signal 312 may be one of the radial axes, e.g., the X-axis 332 or the Z-axis 336 in the configuration shown in FIG. 2. In other examples, control circuit 206 may be configured to analyze up to all three accelerometer axis signals to select an accelerometer axis signal for detecting patient physical activity. For example, the accelerometer axis that produces an activity signal having the greatest difference between an activity metric determined from the activity signal 312 at rest and a patient activity metric determined from the activity signal 312 during non-resting physical activity may be selected by control circuit 206 as the axis for producing the patient physical activity signal 312. Examples of methods that may be used in selecting an accelerometer axis for producing activity signal 312 are generally disclosed in U.S. Patent Application Publication No. 2015/0173655 (Demmer, et al.), incorporated herein by reference in its entirety.

A single axis or a combination of axes may be set as the default axis or axes for producing the cardiac motion signal 310. For instance, the longitudinal axis, corresponding to Y-axis 334 in the configuration illustrated in FIG. 2, may be the default accelerometer axis used for producing cardiac motion signal 310. In other examples, control circuit 206 may be configured to analyze up to all three accelerometer axis signals for selecting the axis or axes used to produce the cardiac motion signal 310. Based on the signal analysis, control circuit 206 may select one, a combination of two or a combination of all three accelerometer axes for producing the cardiac motion signal 310. Example techniques that may be performed by control circuit 206 for selecting which of the accelerometer axes are used to produce the cardiac motion signal are generally disclosed in provisional U.S. Patent Application No. 62/776,034 (Splett, et al.), incorporated herein by reference in its entirety.

In order to reduce the electrical current required to produce cardiac motion signal 310, a single accelerometer axis may be selected as long as the single accelerometer axis signal is determined to produce a relatively high amplitude A4 signal having a signal-to-noise strength deemed reliable for atrial event sensing. If the amplitude of A4 signals from a single axis signal is not deemed reliable for atrial event sensing, control circuit 206 may select a combination of two or all three axes for producing the cardiac motion signal 310. The combination of two or all three axes selected for producing cardiac motion signal 310 may be based on which of the axes produces the highest A4 signal amplitude or at least meets a threshold amplitude requirement that likely promotes reliable A4 signal sensing. The fewest axes required for reliable atrial systolic event sensing may be selected to minimize the current required to produce the cardiac motion signal 310.

The electrical current required to produce both an activity signal 312 and a cardiac motion signal 310 may be reduced when a common accelerometer axis is selected for producing both signals compared to selecting one axis for producing activity signal 312 and selecting one or two different axes for producing cardiac motion signal 310. Accordingly, when two or more axes meet criteria for use as a single axis for producing the cardiac motion signal 310, e.g., by having high A4 amplitude signal strength, and one qualifying axis is the axis that is also selected for producing the activity signal 312, the common, single axis may be selected by control circuit 206 for producing both the cardiac motion signal 310 and the activity signal 312. The sampling control circuit 320 receives the vector selection signal 324 indicating the single axis selected for producing both cardiac motion and activity output signals 310 and 312.

When control circuit 206 selects two axes for producing the cardiac motion signal 310, one of the two axes may be also be selected for producing the activity signal 312. In this way, one remaining non-selected axis of accelerometer 304 may remain disabled (not sampled) by not connecting it to current source 302 as long as the axis is not selected for producing any of the motion output signals 310, 312 and 314. As such, the fewest number of axes that meet signal sensing reliability requirements, e.g., for atrial systolic event sensing and patient activity detection, may be selected by control circuit 206 for producing cardiac motion signal 310 and activity signal 312. Posture signal 314 may be produced from the same axis signal as patient activity signal 312 or any combination of the axes being sampled for producing the cardiac motion and patient activity signals. Electrical current drain may be reduced by selecting the fewest number of axes needed for producing reliable cardiac motion and activity signals, e.g., based on signal amplitude or signal-to-noise ratio.

Sampling control circuit 320 may control sampling of each selected axis of accelerometer 304 individually so that sampling of all three axes is not required during a given time period. Coupling current source 302 simultaneously to all three accelerometer axes 332, 334 and 336 may unnecessarily use current for producing an axis output signal that is not needed. For example, the cardiac motion signal 310 is not necessarily needed during the PVAB period since atrial event sensing does not occur during the PVAB period. An axis may not be selected at all for producing either of the cardiac motion signal 310 or the activity signal 312.

Sampling control of each axis individually by sampling control circuit 320 may include selecting the sampling frequency for each axis of accelerometer 304 according to sampling frequency signal 326 from control circuit 206. A sampled accelerometer axis signal is produced by briefly coupling the current source 302 to the respective axis at time intervals corresponding to the sampling frequency. For instance, current source 302 may be coupled to an accelerometer axis for 1 ms about every 7.8 ms for producing an axis signal sampled at 128 Hz. The sampling frequency of each axis may be selectable between two or more frequencies, e.g., 128 Hz and 256 Hz. In some examples, the default sampling frequency may be 128 Hz since it requires less current than the higher sampling rate of 256 Hz, which requires coupling current source 302 to the accelerometer axis at twice the rate. A higher sampling frequency may be selected, however, for sampling the accelerometer axes selected for producing the cardiac motion signal when the A4 signal to noise amplitude ratio is relatively low. The higher sampling frequency may suppress the noise level promoting more reliable A4 sensing compared to a lower sampling rate.

When a higher sampling frequency is selected for the accelerometer axis (or axes) that are selected for producing the cardiac motion signal 310, the higher sampling rate may be applied only to the axis or axes being selected for producing the cardiac motion signal 310, which may or may not include the axis selected for producing the activity signal 312. When the axis selected for producing the activity signal 312 is not one of the axes selected for producing the cardiac motion signal 310, sampling control circuit 320 may couple current source 302 to the selected activity signal axis at the lower sampling rate, e.g., 128 Hz or about every 8 ms, independent of the higher sampling rate, e.g., 256 Hz or every 4 ms, applied to the accelerometer axis or axes being used for producing the cardiac motion signal 310.

PVAB signal 322 indicates the timing of a ventricular electrical event, paced or sensed, and may be passed to sampling control circuit 320 from control circuit 206 to indicate the starting time of the PVAB period and its duration. In some examples, the duration of the PVAB period may be stored in a register in sampling control circuit 320 such that only the starting time of the PVAB period needs to be passed from control circuit 206 to sampling control circuit 320 on a beat-by-beat basis, at the time of the ventricular electrical event. A signal indicating the starting time of the PVAB period is passed to sampling control circuit 320 in response to each delivered ventricular pacing pulse and each sensed intrinsic R-wave. Since A4 signals are not sensed during the PVAB to avoid oversensing a ventricular event as the atrial systolic event from the cardiac motion signal, sampling of any axis of accelerometer 304 that is selected for producing cardiac motion signal 310 may be suspended, by remaining uncoupled to current source 302, during at least a portion of the PVAB period to conserve electrical current. Individual control of the sampling of each axis allows any axis that is selected only for producing cardiac motion signal 310 to not be sampled during at least a portion of the PVAB period without affecting sampling of any other axis that is selected for producing the activity signal 312 or posture signal 314, either of which may be sampled throughout the PVAB period without interruption in some examples. In other examples, sampling of each axis during the PVAB period may be suspended to conserve electrical current and sample the accelerometer axis signals during ventricular diastole, when ventricular mechanical contraction is not contributing to the motion signal.

ADC 306 receives the sampled analog axis signals from accelerometer 304, e.g., via multiplexor 306, and passes digitized signals to filter 308. In some examples, multiplexer 305 may select each axis signal one at a time for passing an analog signal to ADC 306. For example, if the sampling rate is 128 Hz, sampling control circuit 320 may couple current source 302 to apply electrical current to each selected axis 332, 334 and/or 336 at 7.8 ms intervals. Multiplexer 305 may pass the output signal from each axis during a specified time slot for that sample point. For instance, at every 7.8 ms sampling interval, current source 302 may be coupled to all selected axes for a 1 ms sampling time. Multiplexer 305 may pass the X-axis output signal during a first time slot, e.g. during the first 0.3 ms of the sampling time, the Y-axis output signal during a second, 0.3 ms time slot of the sampling time, and the Z-axis signal during a third, 0.3 ms time slot of the sampling time. Any axis that is not selected for producing a motion signal may produce a zero amplitude output signal that may or may not be passed by multiplexor 305 to ADC 306. In other examples, all three signals from the X-, Y- and Z-axes, if selected, may be passed simultaneously to a respective ADC and on to filter 308 for producing the cardiac motion signal 310, activity signal 312 and optionally posture signal 314.

ADC 306 may receive the PVAB signal 322 indicating the onset of the PVAB period. ADC 306 may be configured to hold the most recently sampled value of each axis signal that is selected for producing cardiac motion signal 310 in response to receiving the PVAB signal 322. The sample point value(s) may be held by ADC 306 during the PVAB period until sampling of all axis signals selected for producing cardiac motion signal 310 is restarted, e.g., just prior to the expiration of the PVAB period.

Filter 308 may include one or more low pass, band pass and/or high pass filters for filtering each of the respective accelerometer axis signals received from ADC 306 to produce the cardiac motion signal 310, activity signal 312 and posture signal 314. For example, the accelerometer axis signal selected for producing patient physical activity signal 312 may be filtered by a 10 Hz low pass filter. The same axis output signal may be filtered by a 1 Hz low pass filter to produce posture signal 314. The 10 Hz low pass filtered signal may be filtered by a 1 Hz high pass filter for producing the activity signal 312 with low, frequency DC components removed. Filter 308 may include a bandpass filter or a combination of high and low pass filters to filter one or more axis output signals selected for producing cardiac motion signal 310. For example, each axis signal may be filtered with a bandpass of 10 to 30 Hz, which may be implemented by a combination of a 10 Hz high pass filter and a 30 Hz low pass filter. The high pass filter may be lowered (e.g., to 5 Hz) if needed to detect atrial event signals that have lower frequency content. In some examples, high pass filtering is performed with no low pass filtering for producing cardiac motion signal 310. In other examples, each accelerometer axis signal selected for producing cardiac motion signal is filtered by a low pass filter, e.g., a 30 Hz low pass filter, with or without high pass filtering. One example of filtering circuitry included in filter 308 is described below in conjunction with FIG. 7.

Each selected x-axis, y-axis and z-axis signal may be filtered for producing a corresponding cardiac motion vector component. When two or all three axis signals are selected for producing the cardiac motion signal 310, the two or more filtered vector signals each corresponding to a respective accelerometer axis may be combined to produce cardiac motion signal 310. For example, electronic interface circuit 301 may include summing circuitry 309. Summing circuitry 309 may rectify each of the incoming filtered cardiac motion vector signals and sum the absolute value of the bandpass filtered sample points of the selected x-, y- and/or z-vector signals to produce cardiac motion signal 310.

Each of cardiac motion signal 310, activity signal 312, and posture signal 314 may be passed to control circuit 206 for use in controlling ventricular pacing delivered by pacemaker 14. As described above, control circuit 206 detects atrial systolic events from the cardiac motion signal 310 for triggering ventricular pacing pulses in an atrial synchronous ventricular pacing mode. Control circuit 206 determines a patient activity metric from activity signal 312 for determining when ventricular rate support is needed during patient activity and for determining the SIR for setting a temporary lower rate ventricular pacing interval. In some examples, posture signal 314 may be used by control circuit 206 for detecting patient posture, which may be used in monitoring the patient for verifying or detecting a condition of the patient or determining that operating parameter adjustment, such as sensing control parameters, may be warranted.

Figure 7:
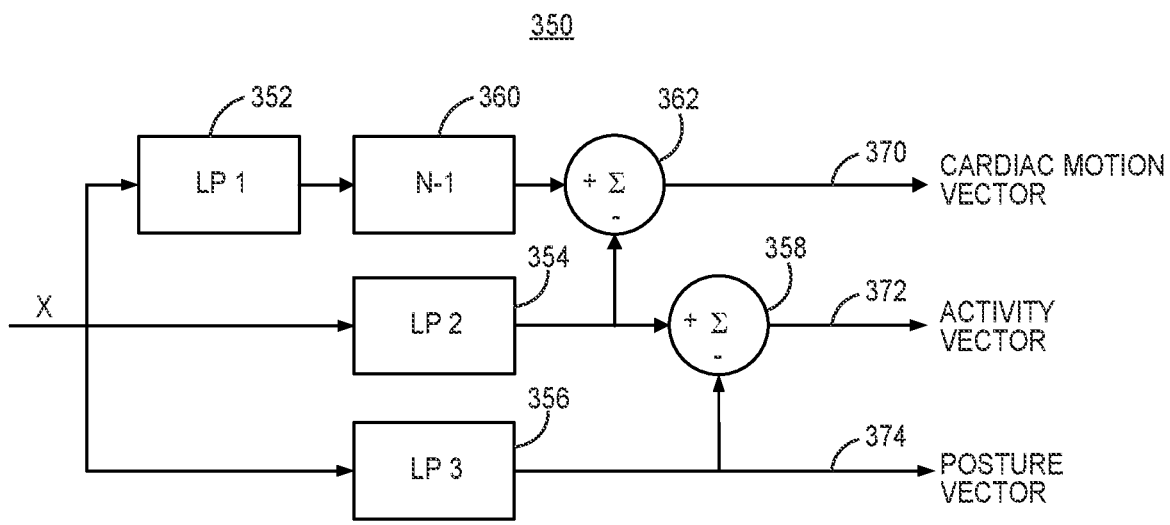
FIG. 7 is a diagram of one example of a filter channel that may be included in the motion sensing circuit of FIG. 6.

FIG. 7 is a conceptual diagram of a filtering channel 350 that may be included in filter 308 of electronic interface circuit 301 in FIG. 6. A filtering channel 350 may be provided for each axis of the accelerometer 304 to produce a filtered vector signal from each accelerometer axis. Moreover, each filtering channel may perform different filtering of the incoming accelerometer axis signal for producing multiple different filtered vector signals for a given axis for producing each of the cardiac motion signal, the activity signal and/or the posture signal. The conceptual diagram of FIG. 7 is an example of one filtering channel 350 of filter 308. In the example shown, the sampled X-axis accelerometer signal is shown as input as an example; however the filter channel 350 may be replicated to provide three filter channels for receiving and filtering each of the x-axis, y-axis and z-axis signals.

The axis signal is provided as input to a first low pass filter (LP1) 352, a second low pass filter (LP2) 354 and a third low pass filter (LP3) 356. In one example, LP1 352 is a 30 Hz low pass filter, LP2 354 is a 10 Hz low pass filter, and LP 3 356 is a 1 Hz low pass filter. The 30 Hz low pass filtered signal from LP1 352 may be delayed by a delay circuit 360, to account for any delays between the output of LP1 352 and LP2 354. For instance, LP2 354 may be a two-stage finite impulse response (FIR) moving average filter that may introduce a phase delay of up to 3 sample points. LP1 352 filter may be implemented in parallel with a first stage of LP2 354 as a FIR moving average filter that introduces up to at least 1 sample point delay. Delay circuit 360 may provide the additional phase delay of up to 2 sample points of the 30 Hz low pass signal to equalize the phase delay of the LP1 and LP2 filtered signal outputs.

The delayed, 30 Hz low pass filtered signal from LP1 352 is passed to summation circuit 362. The 10 Hz low pass filtered signal from LP2 354 is subtracted from the delayed 30 Hz low pass filtered signal by summation circuit 362, e.g., using a spectral inversion technique, to produce a 10-30 Hz bandpass filtered cardiac motion vector signal 370. This vector signal may be the x-axis cardiac motion vector signal that is received by summation circuitry 309 of FIG. 6, which combines one or more x-, y- and z-cardiac motion vector signals received from respective filtering channels of filter 308 to produce the cardiac motion signal 310 that is output to control circuit 206.

The 1 Hz low pass filtered signal from LP3 356, which may be an infinite impulse response (IIR) single-order filter, may be subtracted from the 10 Hz low pass filtered signal from LP2 354 by summation circuit 358 to produce the 1-10 Hz bandpass filtered patient activity vector signal 372. Alternatively, filter channel 350 may include a 1 Hz high pass filter, and the 10 Hz low pass filtered signal from LP2 354 may be passed through a 1 Hz high pass to provide a 1-10 Hz bandpass filtered patient activity vector signal 372. The 1 Hz low pass filtered signal from LP3 356 may be produced as a posture vector signal 374. Each of the activity vector signal 372 and the posture vector signal 374 may be passed directly to control circuit 206 without being combined with any other vector signal in some examples. In other examples, two or more vector signals may be combined to produce the patient physical activity signal 312 and the patient posture signal 314 that are output to control circuit 206. Depending on which accelerometer axis signals are selected for producing the respective cardiac motion signal 310, activity signal 312 and posture signal 314, not all filtered vector signals produced by a given filtering channel 350 are necessarily used in producing the respective output signals 310, 312 and 314.

Cardiac motion signals are generally expected in the 10 to 30 Hz range and patient activity signals are generally expected to be 10 Hz or less. However, the specific cut-off frequencies of LP1 352, LP2 354 and LP3 356 may be higher or lower than the examples given above to produce the cardiac motion vector signal 370, activity vector signal 372 and posture vector signal 374. By subtracting the output of LP2 354 from the delayed output of LP1 352, an additional filter stage required to produce the bandpass filtered cardiac motion vector signal 370 can be eliminated. Current drain from power source 214 is reduced by eliminating an additional 10 Hz high pass filter stage for producing the 10-30 Hz bandpass filtered signal and routing capacitance is reduced in each of the three filtering channels of filter 308 for producing all three x-, y- and z-cardiac motion vector signals as needed.

An additional high pass filter stage required for producing the cardiac motion vector signal 370 may also add delay in the signal output. The ventricular pacing pulse may need to be delivered relatively quickly after detecting the A4 event in order to achieve desired mechanical synchrony between the atrial and ventricular contractions. For example, the AV delay may be as short as 10 to 20 ms. Accordingly, eliminating a high pass filter stage by subtracting the output of LP2 354 from LP1 352 reduces the delay introduced by the filtering channel 350, increasing the time accuracy of A4 event detection and reducing the response time for synchronizing the ventricular pacing pulse to the detected A4 event.

In some instances, the patient physical activity vector 372 and posture vector 374 produced by a given filter channel may be unused by the motion sensing circuit 212 in producing the activity signal 312 and the posture signal 314, respectively, or the cardiac motion vector signal 370 may be unused in producing the cardiac motion signal 310. For example, the x-axis of the accelerometer 304 may be selected only for producing the activity signal 312 so that the activity vector signal 372 from the x-axis filter channel 350 is output as the patient physical activity signal 312. The cardiac motion vector signal produced by a y-axis filter channel (which may be a replicate of filter channel 350) may be the only axis signal selected to produce the cardiac motion signal 310, in which case the cardiac motion vector signal 370 produced by the x-axis filter channel 350 may be unused. In this case, sampling of the y-axis signal may be suspended during at least a portion of the PVAB period. Sampling of the x-axis signal may or may not be suspended during the PVAB period.

In other examples, when a single axis is selected for producing both the cardiac motion signal and the activity signal, the cardiac motion vector signal may be output as the cardiac motion signal 310, and the activity vector signal may be output as the activity signal 312, both produced by a single filter channel. In this case, the sampling of the single axis signal may still be suspended during at least a portion of the PVAB period to conserve electrical current. The patient activity metric may be determined by the control circuit from the activity signal that is produced over discontinuous sampling periods, primarily outside the PVAB period. In this way, motion signals due to ventricular contraction may be removed from the activity signal, which may improve the accuracy of the activity metric.

Figure 8:
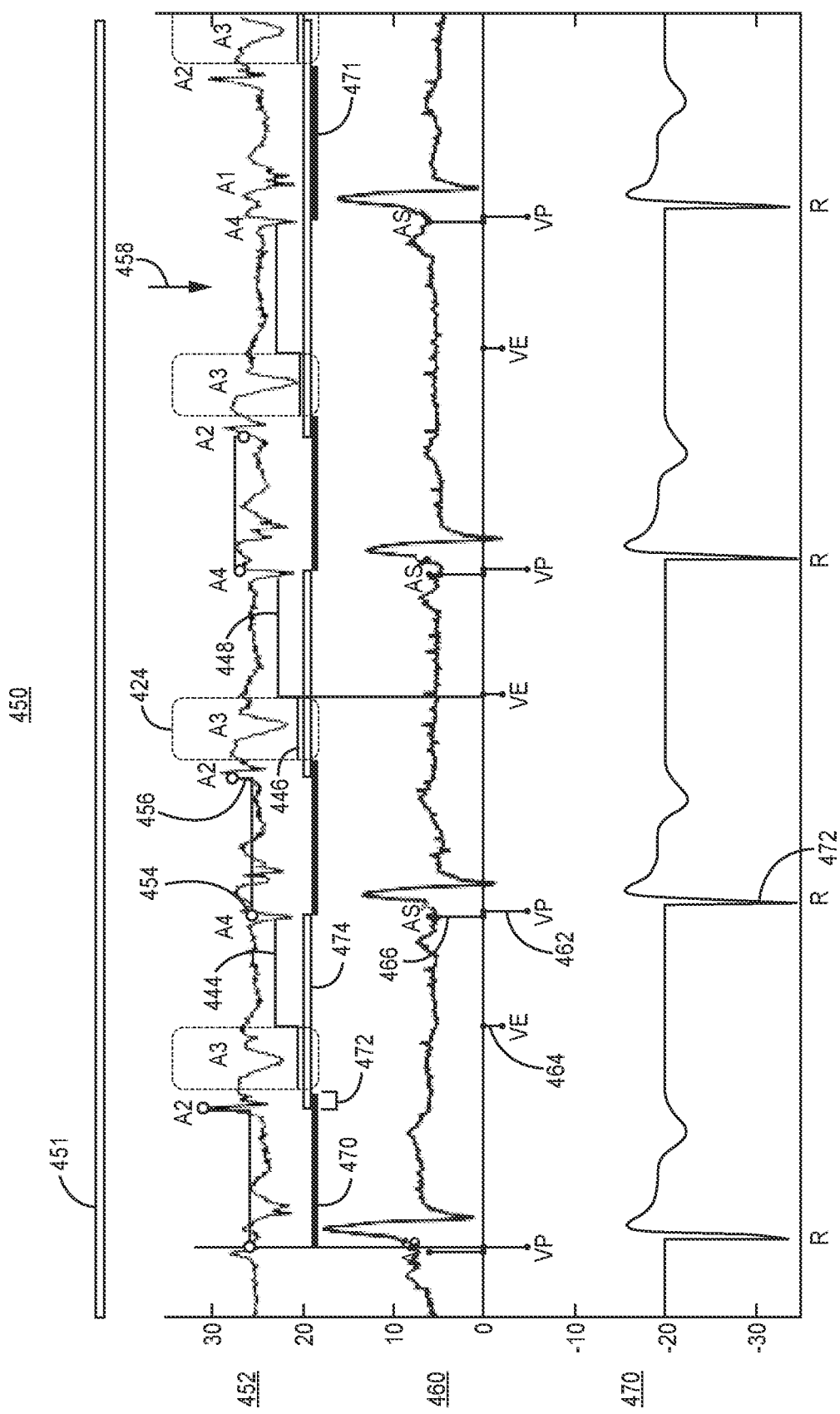
FIG. 8 depicts a cardiac motion signal that may be produced by the motion sensing circuit of FIG. 6.

FIG. 8 depicts a cardiac motion signal 450 that may be produced by motion sensing circuit 212, a ventricular EGM signal 456 that may be produced by cardiac electrical signal sensing circuit 204, and an ECG signal 454 including cardiac event markers. As described above, control circuit 206 may pass a PVAB signal to motion sensing circuit 212 to indicate the occurrence of a ventricular electrical event, either a sensed intrinsic R-wave or a delivered ventricular pacing pulse 462 as in the example of FIG. 8. The PVAB period 470 extends from the ventricular pacing pulse 462 until a starting time of A3 window 424. In response to receiving the PVAB signal, motion sensing circuit 212 samples and holds a most recently sampled value 454 of each accelerometer axis signal that is selected for producing cardiac motion signal 452. The motion sensing circuit 212 holds the value of sample 454 during the PVAB period 470, while sampling of the accelerometer axis signal is suspended.

In some examples, an axis signal that is used only for producing cardiac motion signal 452, and is not being used for producing the activity signal, is sampled and held during PVAB period 470. Sampling of any axis signal that is used to produce the activity signal and/or posture signal, and may or may not be used to produce the cardiac motion signal, may continue during the PVAB period 470 without interruption. In other examples, all axis signals that are used for producing cardiac motion signal 470, whether used for producing the activity signal and/or posture signal or not, are held at a most recently sampled value 454 during the PVAB period 470.

The motion sensing circuit 212 may resume sampling of the accelerometer axis signal(s) not being sampled during PVAB period 470 at the start of a filter settling time 472 earlier than the expiration of PVAB period 470. In this way, sampling control circuit 212 limits sampling of any accelerometer axis signal used for producing cardiac motion signal 452 to a sampling window 474 to conserve electrical current required to produce cardiac motion signal 452. Sampling window 474 extends from the start of filter settling time 472, just prior to the expiration of the PVAB period 470, until an A4 event is sensed or the next ventricular electrical event (and corresponding PVAB signal).

Cardiac motion signal 452 is produced during the sampling window 474 but is held at the most recently sampled value, e.g., sample point 454, from the start of the PVAB period until the end of the PVAB period less the filter setting time 472. At the start of sampling window 474, filter 308 (FIG. 6) will receive a step input 456 as the signal input to filter 308 changes from the held sample point value 454 to the first sample point 456 of sampling window 474. The filter settling time 472 is a selected time interval that allows the output signal of filter 308 to settle from the step input 456 to within an acceptable percentage of the actual motion signal. In one example, filter settling time 472 is about 70 ms, e.g., for the filter channel 350 shown in FIG. 7. After the settling time 472, the cardiac motion signal 452 output from motion sensing circuit 212 to atrial event detector circuit 240 is reliable for detecting A4 signals.

In the example shown in FIG. 8, the cardiac motion signal 452 is not rectified so the A3 and A4 signals are seen to be negative-going peaks. As such, the A4 sensing threshold 444 is shown as a negative threshold amplitude that has a greater absolute amplitude 446 during A3 window 424 than the absolute amplitude 448 after the ending time of A3 window 424. The A3 window ending time may be denoted on a marker channel by an ending time maker (VE) 464 as shown on ECG signal 460.

The earliest crossing of the A4 sensing threshold 444 after PVAB period 470 expires is detected as the atrial systolic event, as indicated by the atrial sense (AS) markers 466 on ECG signal 460. In response to an A4 signal detection by control circuit 206, pulse generator 202 generates a ventricular pacing pulse 462 at an AV interval. The AV interval may be a programmed value selected by a clinician and is the time interval from the detection of the atrial event until delivery of the ventricular pacing pulse. The AV interval may be identified as being hemodynamically optimal for a given patient based on clinical testing or assessments of the patient or based on clinical data from a population of patients. The AV interval may be determined to be optimal based on relative timing of electrical and mechanical events as identified from the ECG signal 460, EGM signal 470 and motion sensor signal 452. The AV interval may be set relatively short, e.g., at 10 to 50 ms in some examples, to control pulse generator 202 to deliver a ventricular pacing pulse relatively quickly after the atrial systolic mechanical event since the ventricular mechanical contraction is delayed following the pacing evoked R-wave 472.

In some examples, signals shown in FIG. 8 may be shown in a display generated by external device 20 during a telemetry mode (in real time) or following an interrogation session to allow a clinician to view cardiac motion signal 452 and cardiac event markers relative to the EGM signal 456 and ECG signal 454. In order for a complete display of the cardiac motion signal 452 to be generated for display by external device 20, control circuit 206 may signal motion sensing circuit 212 to withhold suspending the sampling of any axis during the telemetry mode. In the example of FIG. 8, control circuit 206 detects a telemetry mode at arrow 458. The telemetry mode may be detected in response to the actuation of a reed switch 246 (FIG. 3) or other actuated switch, e.g., by holding a magnet or programming head over pacemaker 14.

In response to determining that the telemetry mode is in effect, control circuit 206 may pass a telemetry mode signal to sampling control circuit 320. In response to receiving the telemetry mode signal, control circuit 320 enables sampling of all selected cardiac motion signal axes throughout the PVAB period 470. As shown in FIG. 8, the cardiac motion signal 452 is produced during the last PVAB period 471 shown so that the cardiac motion signal 452 can be transmitted to external device 20 for producing a display of the cardiac motion signal 452 that includes A1, A2, A3 and A4 signals throughout the cardiac cycle without interruption.

Figure 9:
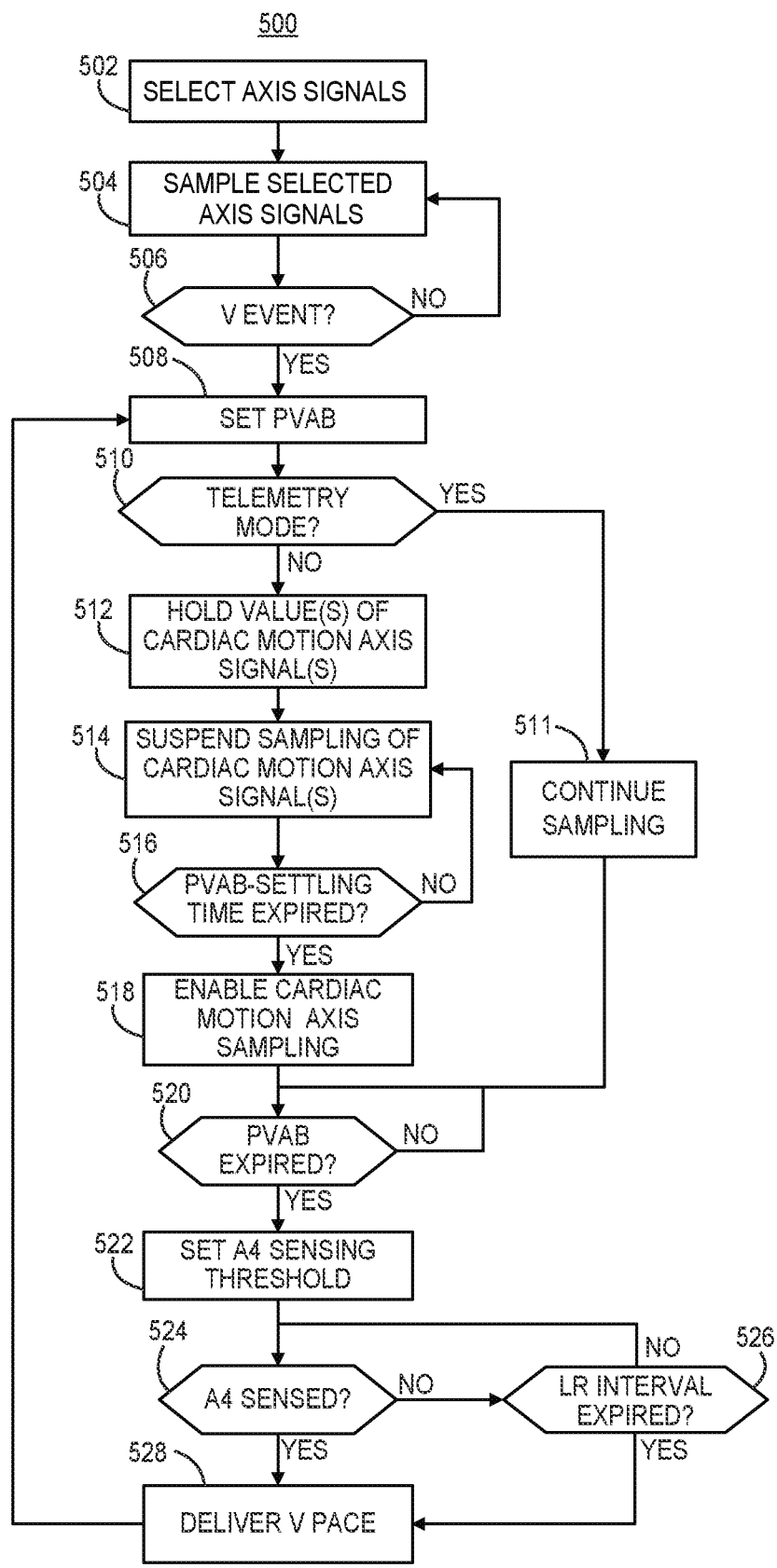
FIG. 9 is a flow chart of a method performed by the pacemaker of FIG. 1 for producing a cardiac motion signal and controlling atrial synchronous ventricular pacing according to one example.

FIG. 9 is a flow chart 500 of a method performed by pacemaker 14 for producing a cardiac motion signal and controlling atrial synchronous ventricular pacing. At block 502, control circuit 206 selects the accelerometer axes to be used for producing the cardiac motion signal and the activity signal (and optionally a posture signal). Selection of the accelerometer axes for use in producing motion signals may be based on analysis of each axis signal and predetermined criteria for selecting axis signals or may be default or user programmed axis selections. A single axis of the accelerometer or a combination of two or all three axis signals may be selected for producing the cardiac motion signal. The activity signal vector is generally a single axis of the accelerometer but in other examples could be a combination of two or more axes.

The accelerometer axes selected for producing the cardiac motion signal and the activity signal are sampled at block 504 by coupling the current source of motion sensing circuit 212 to each of the selected axes at the sampling frequency. In one example, current is applied to the selected axes for about one millisecond every eight milliseconds to produce motion signals sampled at 128 Hz. If any of the accelerometer axes are not selected for producing the cardiac motion and activity signals, electrical current is withheld from the non-selected axis to minimize current drain without interfering with the sampling of the selected axis or axes. For example, with reference to FIG. 6, if the X-axis 332 is selected for producing the activity signal and the X- and Y-axes 332 and 334 are selected for producing the cardiac motion signal, sampling control circuit 320 may withhold coupling current source 302 to the Z-axis 336 of accelerometer 304.

When a ventricular electrical event (pacing pulse or sensed R-wave) occurs at block 506, control circuit 206 signals the motion sensing circuit 212 to set the PVAB period at block 508 for use in controlling sampling of the accelerometer axis signals. As described above, a telemetry mode may be available for transmitting the cardiac motion signal in real time. In this case, at block 510, control circuit 206 may determine if a telemetry mode is in effect before disabling sampling of any selected axis. Control circuit 206 may determine that the telemetry mode is in effect in response to detecting actuation of a reed switch included in pacemaker 14. In other examples, the telemetry mode may be initiated by a user initiated command transmitted by an external device and received by telemetry circuit 208.

The control circuit 206 may respond to the telemetry mode determination by signaling the sampling control circuit 320 (FIG. 6) to cancel withholding accelerometer axis signal sampling during the PVAB period. When the telemetry mode is detected, "yes" branch of block 510, all accelerometer axes selected for producing the cardiac motion signal may continue to be sampled at the selected sampling rate at block 511 throughout the PVAB period. In this way, the cardiac motion signal is produced throughout the cardiac cycle without interruption so that the A1 and A2 signals corresponding to ventricular events may be observed in addition to A3 and A4 events.

The telemetry mode of sampling the accelerometer signals may be optional. In other examples, withholding of sampling of the cardiac motion signal axis or axes may still occur. A transmitted cardiac motion signal may be displayed with a flat or interpolated signal during the PVAB period. In some examples, any axis signal that is sampled throughout the PVAB period because it is also used for producing the activity signal may be used for generating a display of the cardiac motion signal during the PVAB period even when another axis used for producing the cardiac motion signal outside the PVAB period is not sampled during the PVAB period.

If the telemetry mode is not in effect, as determined at block 510, motion sensing circuit 212 may hold a most recently sampled value of one or more axis signals at block 512 then suspend sampling of the axis signal. In some examples, motion sensing circuit 212 holds the most recently sampled value(s) of each axis signal that is selected only for producing the cardiac motion signal but not selected for producing the activity signal. Sampling of the axis or axes that are selected only for producing the cardiac motion signal and not for producing the activity signal may be suspended during the PVAB period at block 514. Sampling is suspended or disabled by withholding electrical current from the accelerometer axis or axes used for producing the cardiac motion signal but may not be suspended for any axis that is used for producing the activity signal or for both the cardiac motion and activity signals. For example, if the activity signal axis is selected to be the X-axis of the accelerometer, and the cardiac motion signal axis is selected to by the sum of the X-axis and the Y-axis signals, the most recently sampled value of the Y-axis signal is held upon starting the PVAB period, and electrical current is withheld from the Y-axis during at least a portion of the PVAB period. Since the X-axis signal is used for producing both the activity signal and the cardiac motion signal, the X-axis signal continues to be sampled during the PVAB period at the selected sampling rate. Electrical current drain of the pacemaker power source 214 is reduced by disabling sampling of any axis that is used only for producing the cardiac motion signal during the PVAB period compared to sampling all selected accelerometer axis signals throughout the PVAB period. Depending on the heart rate, current required to sample an axis used only for producing the cardiac motion signal may be reduced by as much as 50% or more.

At block 516, motion signal 216 determines when the PVAB period less a filtering settling time has expired. The filter settling time is the time needed for the filter of the motion sensing circuit 212 to settle from the step input resulting from the last held value at the start of the PVAB to the next sampled value. By re-initiating sampling of the axis or axes that are disabled during the PVAB period at the settling time earlier than the expiration of the PVAB period, the output of the motion sensing circuit filter is settled and within an acceptable error band, e.g., within 2-5% of the steady-state response, by the expiration of the PVAB period. As such, when the PVAB period less the filtering settling time has expired (block 516), sampling of any disabled axis or axes of the accelerometer is restarted at block 518. By the time the PVAB period expires (block 520), sensing of the A4 event from the bandpass filtered cardiac motion signal can occur without oversensing due to overshoot or artifact in the cardiac motion signal due to the step input that occurs upon restarting sampling of the selected axis signal.

Upon expiration of the PVAB period ("yes" branch of block 520), control circuit 206 sets the A4 sensing threshold that is applied to the cardiac motion signal. The earliest crossing of the A4 sensing threshold amplitude by the cardiac motion signal after the PVAB period expires is sensed as the atrial systolic event at block 524. As described above, the A4 sensing threshold may include a first, higher threshold amplitude during the A3 (passive ventricular filling) window and a second lower threshold amplitude after the A3 window.

In response to the control circuit 206 sensing the A4 signal, a ventricular pacing pulse is triggered at the AV pacing interval at block 528. If the ventricular lower rate (LR) interval expires at block 526 prior to sensing an A4 event at block 524, a ventricular pacing pulse may be delivered at block 528 without sensing an A4 event. It is to be understood that the LR interval that expires at block 526 may be a rate smoothing interval to avoid abrupt changes in ventricular rate. The rate smoothing interval may be based on the actual ventricular rate, which may be a median ventricular pacing rate determined from a most recent predetermined number of ventricular cycles, for example. Upon delivery of a ventricular pacing pulse at block 528, the process returns to block 508 to start the next PVAB period.

It is recognized that in some instances an intrinsic R-wave may be sensed before the atrial systolic event is sensed at block 524 and before the LR interval expires at block 526. While not shown explicitly in FIG. 9, it is to be understood that when an intrinsic R-wave is sensed, the process of FIG. 9 may return to block 508 without delivering a ventricular pacing pulse at block 528, and motion sensing circuit 212 and control circuit 206 may set the next PVAB period at block 508 in response to the sensed R-wave.

Figure 10:
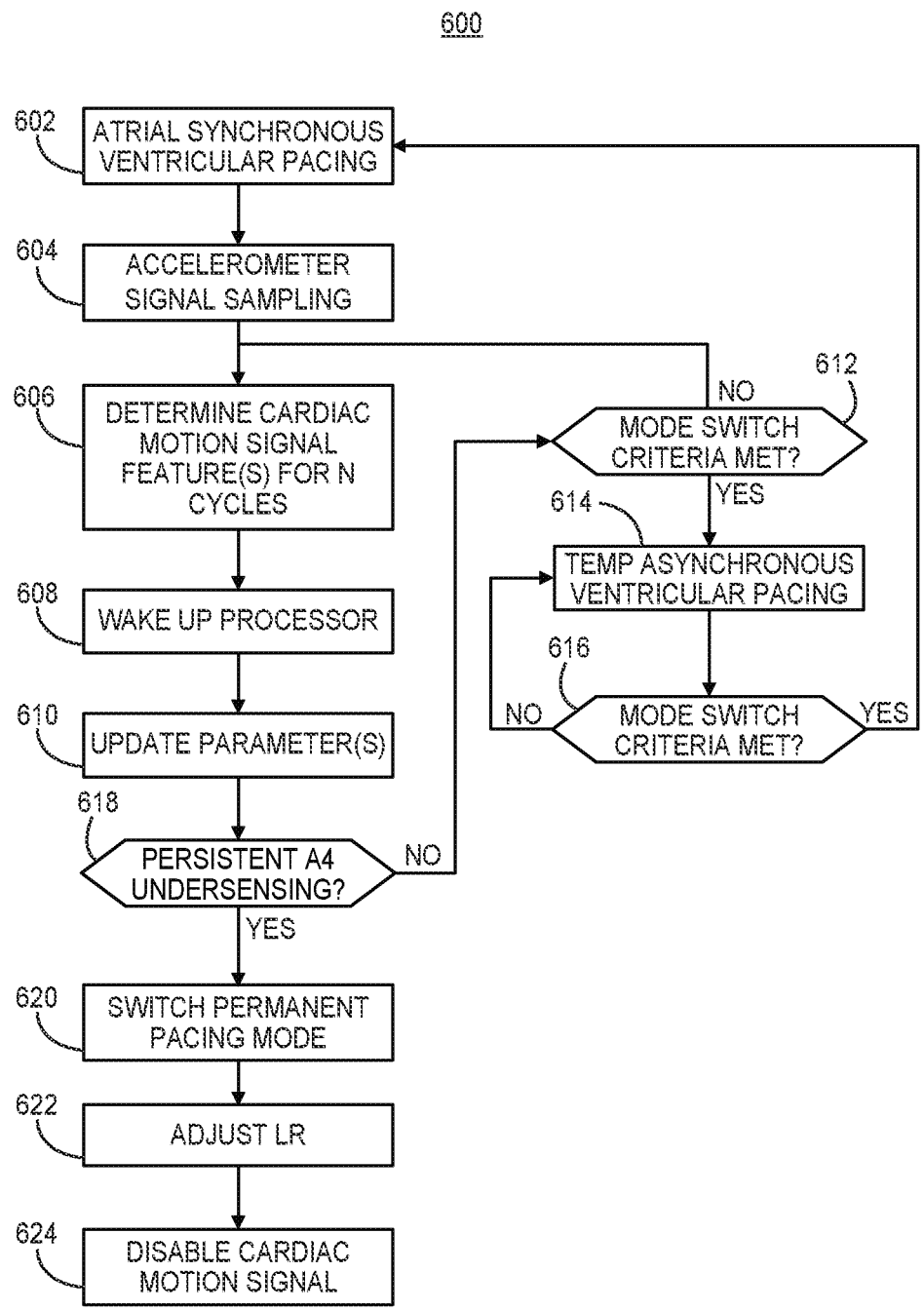
FIG. 10 is a flow chart of a method performed by the pacemaker of FIG. 1 for controlling ventricular pacing according to another example.

FIG. 10 is a flow chart 600 of a method performed by pacemaker 14 for controlling ventricular pacing according to another example. Pacemaker 14 may be configured to deliver atrial synchronous ventricular pacing in a patient that experiences AV conduction block by sensing atrial systolic events from the cardiac motion signal and delivering a ventricular pacing pulse at an AV pacing interval following each sensed atrial systolic event. In some situations, however, an asynchronous ventricular pacing mode may be needed or desired. For example, if the patient is exercising and A4 event sensing from the motion signal becomes unreliable due to increased physical activity signals present in the accelerometer axis signals, the atrial synchronized ventricular pacing rate may not be fast enough to adequately support the patient's metabolic demand. In this case pacemaker 14 may switch to an asynchronous ventricular pacing mode to provide rate responsive ventricular pacing that doesn't track the atrial events, e.g., a VVIR or VDIR pacing mode. When the patient's activity level decreases such that ventricular pacing at an increased rate is no longer needed and atrial event sensing is deemed reliable for atrial synchronous ventricular pacing, control circuit 206 may switch back to the atrial synchronous ventricular pacing mode, e.g., a VDD pacing mode.

In other instances, a patient may have intermittent AV block. Pacemaker 14 may deliver atrial synchronous ventricular pacing during AV block but may switch to an asynchronous ventricular pacing mode periodically to promote AV conduction through the heart's natural intrinsic conduction system. If AV conduction is detected, the pacemaker 14 may remain in the asynchronous ventricular pacing mode until AV conduction block is detected again and then switch back to the atrial synchronous ventricular pacing mode. Accordingly, various mode switching criteria may be applied by control circuit 206 in determining when to switch from the atrial synchronous pacing mode, e.g., a VDD pacing mode, to an asynchronous pacing mode, e.g., VVI(R) or VDI(R), and vice versa.

In the example of FIG. 10, pacemaker 14 is operating in an atrial synchronous ventricular pacing mode at block 602. The atrial synchronous ventricular pacing mode may be the permanently programmed pacing mode of pacemaker 14. The atrial synchronous ventricular pacing mode includes sampling of the accelerometer axis signals at block 604 according to the techniques described above. In particular, one or more accelerometer axis that is selected for producing the cardiac motion signal is not sampled during at least a portion of the PVAB period, e.g., the PVAB period less a filter settling period.

At block 606, one or more features of the cardiac motion signal are determined for a predetermined number (N) of ventricular cycles. Each cardiac motion signal feature is determined during each ventricular cycle outside the PVAB period, e.g., between each of a predetermined number of the PVAB periods. Examples of features that may be determined by hardware of control circuit 206 without waking up processor 244 include a maximum peak amplitude of the cardiac motion signal outside the PVAB period and a time interval from the ventricular electrical event that starts the PVAB period to the maximum peak outside the PVAB period.

At block 608, the control circuit 206 wakes up processor 244 after a predetermined number of ventricular cycles. Processor 244 uses the cardiac motion signal features accumulated over the N ventricular cycles to update atrial event sensing parameters at block 610. Sensing control parameters that may be updated by processor 244 based on the cardiac motion signal features may include the A4 sensing threshold amplitudes applied during the A3 window and after the A3 window and the ending time of the A3 window. In order to conserve power source 214, processor 244 may be powered up for updating sensing control parameters only after a predetermined number of ventricular cycles, e.g., every 8 ventricular cycles, instead of remaining powered up for updating sensing control parameters on a beat-by-beat basis. Other processing functions performed by processor 244 may also be performed only upon wake-up after the predetermined number of ventricular cycles. Other processing functions may include, as examples, device diagnostics, updating a paced event counter, updating sensed event counters, updating a counter of ventricular pacing pulses triggered by a sensed A4 event and updating a counter of ventricular pacing pulses that were delivered in the absence of a sensed A4 event. In some examples, an A4 sensing counter is increased each time a ventricular electrical event, which may include ventricular pacing pulses and/or sensed intrinsic R-waves, is appropriately preceded by a sensed A4 event during the ventricular cycle. An A4 undersensing counter is increased each time a ventricular electrical event, paced and/or sensed, is not preceded by a sensed A4 event during the ventricular cycle.

At block 618, processor 244 may determine if persistent undersensing of the A4 event is detected. The value of the A4 sensing counter and the value of the A4 undersensing counter may each be compared to a respective threshold. Additionally or alternatively, the difference between or ratio of these A4 sensing and A4 undersensing counter values may be compared to a threshold. If a threshold percentage of delivered ventricular pacing pulses (or all ventricular electrical events) are not preceded by or triggered by a sensed A4 event, A4 undersensing may be occurring. Persistent atrial event undersensing may be detected in response to a threshold percentage of the ventricular pacing pulses being delivered in the absence of a sensed A4 event over a predetermined time interval. For example, if 70%, 80% or other threshold percentage of ventricular pacing pulses (or all ventricular paced and sensed events) occur during the atrial synchronous ventricular pacing mode without an A4 event being sensed, persistent atrial undersensing may be detected at block 618.

Various criteria may be defined for detecting persistent atrial event undersensing at block 618. For instance, if a threshold percentage of ventricular pacing pulses delivered over 24 hours (or all ventricular electrical events, sensed or paced) occur in the absence of a corresponding sensed A4 event for at least 14 consecutive days, or other predefined threshold number of consecutive or non-consecutive days or weeks, persistent atrial event undersensing may be detected. Additionally, the criteria for detecting persistent A4 undersensing applied by control circuit 206 at block 618 may require that the atrial synchronous pacing mode be in effect at least a majority of the time before persistent A4 undersensing can be ascertained. In some cases, a temporary asynchronous pacing mode with or without rate responsive pacing may be in effect a majority of the time over a given 24-hour period or predetermined number of days or weeks over which A4 undersensing is being evaluated. A temporary asynchronous ventricular pacing mode may be in effect for extended periods of time due to detection of AV conduction or a need for ventricular rate support due to patient physical activity, for example, as further described below in conjunction with blocks 612 and 614. When the atrial synchronous pacing mode has not been in effect at least a majority of the time (or at least another predefined threshold percentage of time, e.g., 40% of the time, 50% of the time, 60% of the time, etc.) over each 24 hour period or over the required number of days or weeks over which A4 undersensing is being evaluated, persistent A4 undersensing is not detected at block 618. In some examples, therefore, even if other A4 undersensing criteria are satisfied, e.g., based on the values reached by the A4 undersensing counter and the A4 sensing counter over a given time period, the persistent A4 undersensing detection criteria are not met at block 618 when the atrial synchronous ventricular pacing mode has been in effect less than a threshold portion of the given time period. In another illustrative example, if a temporary asynchronous ventricular pacing mode is in effect for a majority of a given twenty-four hour period, persistent A4 undersensing criteria are not satisfied for that twenty-four hour period. A4 undersensing may not be detected for any two week period that includes that twenty-four hour period.

When undersensing of the A4 event is persistent, electrical current used by the motion sensing circuit 212 for producing the cardiac motion signal for atrial event sensing may be an inefficient use of the pacemaker power source 214. As such, control circuit 206 may perform one or more actions based on A4 undersensing being persistent. For example, control circuit 206 may generate an alert that indicates that A4 undersensing is persistent. Telemetry circuit 208 may transmit the alert to an external device, e.g., to indicate to a physician that A4 undersensing is persistent.

In another example, based on determining that A4 undersensing is persistent, control circuit 206 may switch the pacing mode from the permanent atrial synchronous ventricular pacing mode to a permanent asynchronous pacing mode at block 620. In this way, control circuit 206 will not automatically switch back to the atrial synchronous pacing mode unless manually reprogrammed by a user. The switch to the permanent asynchronous pacing mode at block 620 may be a switch from a VDD pacing mode to VVI(R), for example, with atrial event detector circuit 240 disabled.

At block 622, control circuit 206 may adjust the programmed lower pacing rate used during the permanent asynchronous ventricular pacing mode. The lower pacing rate may be set to a different lower rate than that used during a temporary asynchronous ventricular pacing mode or during the permanent atrial synchronous pacing mode. For example, if the lower rate is set relatively low, e.g., 40 pulses per minute, to promote AV conduction, the lower rate may be adjusted to a higher rate, e.g., 60 pulses per minute, to promote an adequate resting heart rate during the permanent asynchronous ventricular pacing mode.

At block 624, control circuit 206 may disable sampling of any accelerometer axis signal used only for producing the cardiac motion signal as long as the permanent asynchronous pacing mode is in effect to conserve the pacemaker power source. The vector selection signal from control circuit 206 to sampling control circuit 320 of motion sensing circuit 212 (see FIG. 6) may include a single accelerometer axis for producing the activity signal with no axes selected for producing the cardiac motion signal during the permanent asynchronous pacing mode. As such, sampling control circuit 320 couples current source 302 only to the axis selected for producing the activity signal. By switching to a permanent asynchronous pacing mode with atrial event detection and cardiac motion signal production disabled, the power source 214 of pacemaker 14 may be conserved to provide asynchronous ventricular pacing for a longer useful life of the pacemaker than if the cardiac motion signal continues to be produced. The activity signal may continue to be produced by motion sensing circuit 212 after switching to the permanent asynchronous ventricular pacing mode to detect a need for rate responsive pacing to support patient physical activity.

Referring again to block 618, when criteria for detecting persistent A4 undersensing are not satisfied, "no" branch of block 618, the processor 244 may determine if temporary mode switching criteria are met at block 612. Criteria for switching from the permanent atrial synchronous pacing mode to a temporary asynchronous pacing mode may be based on the number or rate of sensed atrial events, the patient activity level, the actual ventricular rate (including paced and any intrinsic beats) or any combination thereof. Examples of mode switching criteria that may be applied at block 612 are generally disclosed in U.S. Pat. No. 9,399,140 (Cho, et al.) and in U.S. Pat. Publication No. 2018/0154154 (Sheldon, et al.).

When mode switching criteria are met, "yes" branch of block 612, control circuit 206 temporarily switches to an asynchronous ventricular pacing mode at block 614. In some instances, control circuit 206 may switch to a temporary rate responsive pacing mode to provide ventricular rate support during increased patient physical activity as determined from the activity signal. In this case, when the patient activity level decreases again, e.g., to a resting state or below an activities of daily living threshold, criteria for switching back to the permanent atrial synchronous ventricular pacing mode may be satisfied at block 616. Accelerometer signal sampling may be controlled according to the techniques disclosed above throughout the rate responsive asynchronous ventricular pacing mode, including sampling of the axis or axes selected for producing the cardiac motion signal, e.g., in a VDIR pacing mode. During the rate responsive asynchronous ventricular pacing mode, the cardiac motion signal features may continue to be determined so that atrial systolic event sensing parameters can be updated on every $8^{th}$ ventricular cycle (or other predetermined number). In this way, when mode switching criteria are met for returning to the atrial synchronous ventricular pacing mode, sensing control parameters for detecting A4 events are updated for promoting reliable A4 sensing immediately upon returning to the atrial synchronous ventricular pacing mode. In other examples, sampling of any axis used only for producing the cardiac motion signal may be suspended to reduce current drain during the rate responsive pacing mode, e.g., in a VVIR pacing mode. Only the axis used for producing the activity signal may be sampled to provide an updated SIR during the rate responsive pacing mode and for determining when the pacing mode can be switched back to the atrial synchronous ventricular pacing mode based on reduced patient activity.

At other times, mode switching criteria may be met at block 612 when an AV conduction check timer expires. Control circuit 206 may switch from the permanent atrial synchronous ventricular pacing mode to a temporary asynchronous ventricular pacing mode to promote intrinsic conduction of the atrial depolarization to the ventricles to reduce the frequency of ventricular pacing. The lower pacing rate in the temporary asynchronous ventricular pacing mode may be set to a relatively low rate, e.g., 40 pulses per minute, to promote AV conduction with minimum ventricular pacing. During the temporary asynchronous ventricular pacing mode, control circuit 206 monitors for evidence of AV block. If AV block is detected, criteria for switching back to the atrial synchronous ventricular pacing mode are satisfied at block 616 ("yes" branch return to block 602).

AV block may be detected based on a threshold number of consecutive or non-consecutive ventricular pacing pulses being delivered at the programmed lower rate due to expiration of the lower rate pacing interval without an intrinsic R-wave being sensed by sensing circuit 204. For example, if at least two out of four ventricular cycles are paced ventricular cycles, the patient may be experiencing AV block. Mode switch criteria are met at block 616, and control circuit 206 switches back to the atrial synchronous ventricular pacing mode at block 602. AV block may be detected only based on ventricular events without requiring the cardiac motion signal for detecting atrial events. As such, during this temporary asynchronous ventricular pacing mode, control circuit 206 may control motion sensing circuit 212 to suspend sampling of any accelerometer axis signal that is used only for producing the cardiac motion signal to conserve the pacemaker power source.

Figure 11:
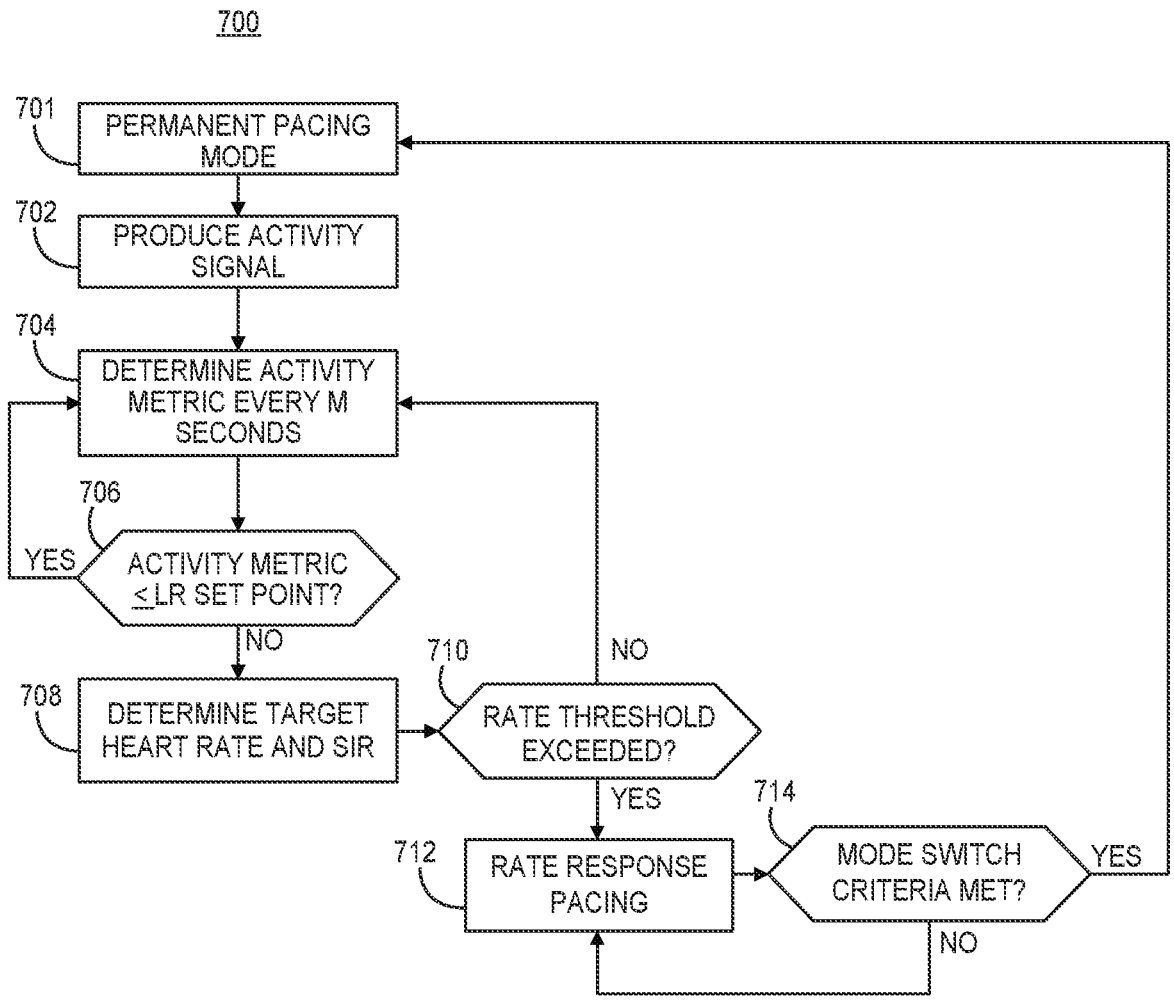
FIG. 11 is a flow chart of a method performed by the pacemaker of FIG. 1 for controlling ventricular pacing according to yet another example.

FIG. 11 is a flow chart 700 of a method performed by pacemaker 14 for conserving power source 214 according to another example. At block 701, pacemaker 14 operates in the permanent pacing mode, which may be an atrial synchronous ventricular pacing mode with atrial event sensing or an asynchronous pacing mode, e.g., VDI or VVI pacing mode. At block 702, motion sensing circuit 212 produces the patient physical activity signal, e.g., by coupling the current source to a selected accelerometer axis at a sampling frequency to produce a sampled activity signal. Control circuit 206 may be configured to receive the activity signal and produce an activity metric every M seconds, e.g., every two seconds, or other predetermined time interval at block 704. The activity metric may be an integral or summation of the activity signal sample points over a two-second time interval in some examples, and may therefore be produced by hardware circuitry of control circuit 206 that does not require processor 244 to be powered up. In other examples, the activity metric may be a count of activity signal sample points that exceed a threshold amplitude during a two-second time interval, which may also be implemented using a comparator and a counter in hardware circuitry included in control circuit 206.

At block 706, control circuit 206 may compare the activity metric to a lower rate set point. The lower rate set point establishes a level of the activity metric determined from the activity signal below which sensed activity is expected to be due largely to heart motion and not an indication of increased metabolic demand due to physical activity. Comparison of the lower rate set point to the activity metric may be performed by a comparator implement in hardware circuitry of control circuit 206 so that processor 244 is not required to be powered up to determine if the activity metric is greater than the lower rate set point. When the activity metric is less than or equal to the lower rate (LR) set point ("yes" branch of block 706), control circuit 206 may withhold determination of a sensor indicated pacing rate. Rather than determining the SIR at each M second interval, pacemaker 14 may determine the SIR only in response to an activity metric that is greater than the lower rate set point.

As such, when the activity metric is greater than the LR set point ("no" branch of block 706), control circuit 206 may wake up processor 244 to determine a target heart rate based on the patient's activity metric and a corresponding SIR that provides rate smoothing from the current ventricular rate to the target heart rate. At block 710, control circuit 206 may determine if mode switching criteria are met based at least in part on the target heart rate determined from the activity metric. In one example, the target heart rate is compared to a threshold rate at block 710. The threshold rate may be based on the actual ventricular rate (which may include paced and sensed ventricular events). If the target heart rate based on the activity metric is much greater than the actual ventricular rate, e.g., at least 20 pulses per minute greater than the actual ventricular rate, control circuit 206 may switch to a temporary rate responsive, asynchronous ventricular pacing mode at block 712. In other examples, other criteria based on the patient activity metric, target heart rate, SIR, rate of sensed A4 events, and/or actual ventricular rate may be used to determine if rate responsive pacing is needed at block 710.

During rate responsive pacing at block 712, control circuit 206 may wake up processor 244 after each M second interval to determine a new SIR using the most recently determined patient activity metric. Ventricular pacing is provided at the SIR, asynchronous to atrial systolic events. In some examples, the accelerometer axis signals used only for producing the cardiac motion signal are not sampled at all during the rate responsive pacing mode. In other examples, the accelerometer axis signals used for producing the cardiac motion signal continue to be sampled during the rate responsive pacing mode according to the sampling control techniques disclosed herein so that automatic updating of the sensing control parameters based on cardiac motion signal features can continue during the rate responsive pacing mode.

The new patient activity metric, and corresponding target heart rate and SIR may also be used to determine when rate responsive pacing is no longer needed due to a decrease in patient activity at block 714. When criteria for switching back to the permanent ventricular pacing mode are satisfied, control circuit 206 switches the pacing mode from the temporary rate responsive pacing mode back to the permanent pacing mode (return to block 701). Since a patient is generally at a resting level a greater portion of the day than at a high enough level of activity that warrants rate responsive pacing, power source 214 is conserved by not using processing power to determine and update the SIR in response to every activity metric, determined every M seconds, during the permanent ventricular pacing mode. For example, if the permanent pacing mode is the atrial synchronous ventricular pacing mode, the processor 244 may be powered up to determine the SIR only when the activity metric is greater than a threshold activity level, which may indicate that a need for switching to a temporary rate responsive pacing mode may be imminent. As long as the patient activity metric is less than the threshold activity level, processing power is conserved by withholding determination of the target heart rate and SIR based on the activity metric compared to the processing power required to determine the target heart rate and SIR after every patient activity metric determination, e.g., after every 2-second interval.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising:
a motion sensing circuit comprising a motion sensor for sensing a motion signal, the motion sensor having a plurality of axes, each axis of the plurality of axes configured to produce an axis signal, the motion sensing circuit configured to sense the motion signal by:
sampling at least one axis signal of the motion sensor;
starting a blanking period corresponding to a portion of a cardiac cycle, the blanking period having an expiration time;
suspending sampling of the at least one axis signal of the motion sensor during at least a portion of the blanking period that is less than an entirety of the blanking period; and
restarting the sampling of the at least one axis signal during the blanking period and before the expiration time of the blanking period;
a control circuit configured to:
receive the motion signal;
detect a cardiac event from the motion signal after the expiration time of the blanking period; and
a pulse generator configured to generate a pacing pulse in response to the control circuit detecting the cardiac event from the motion signal.

2. The medical device of claim 1, wherein:
the control circuit is further configured to:
detect the cardiac event by detecting an atrial event from the motion signal; and
set an atrioventricular pacing interval in response to detecting the atrial event; and
the pulse generator is configured to generate the pacing pulse at the atrioventricular pacing interval following the detected atrial event.

3. The medical device of claim 1, wherein:
the control circuit is further configured to identify a cardiac electrical event; and
the motion sensing circuit is configured to:
start the blanking period in response to the cardiac electrical event; and
suspend the sampling of the at least one axis signal in response to starting the blanking period.

4. The medical device of claim 1, wherein the motion sensing circuit comprises a filter having a settling time, the motion sensing circuit being configured to restart the sampling of the first signal at the settling time earlier than the expiration of the blanking period.

5. The medical device of claim 1, further comprising a processor, wherein:
the control circuit is configured to:
determine a feature of the motion signal produced by the motion sensing circuit between each of a predetermined number of the blanking periods; and
wake up the processor after the predetermined number of blanking periods; and
the processor is configured to determine a cardiac event sensing control parameter used for detecting the cardiac event from the motion signal based on the determined features in response to being woken up.

6. The medical device of claim 1, wherein the motion sensing circuit is further configured to sense the motion signal by sampling the at least one axis signal and a second axis signal of the motion sensor.

7. The medical device of claim 6, wherein the motion sensing circuit is further configured to sample the second axis signal throughout the blanking period.

8. The medical device of claim 7, wherein the motion sensing circuit is further configured to produce a patient physical activity signal from the second axis signal.

9. The medical device of claim 1, further comprising:
a housing that encloses the motion sensor, the control circuit and the pulse generator; and at least one leadless electrode on the housing for delivering the generated pacing pulse.

10. A medical device comprising:
a motion sensor having a plurality of axes, each axis of the plurality of axes associated with an axis signal;
circuitry in communication with the motion sensor, the circuitry configured to:
sample at least one axis signal of the motion sensor;
start a blanking period corresponding to a portion of a cardiac cycle, the blanking period having an expiration time;
suspend sampling of the at least one axis signal during at least a portion of the blanking period that is less than an entirety of the blanking period; and
restart the sampling of the at least one axis signal during the blanking period and before the expiration time of the blanking period;
receive a motion signal from the motion sensor, the motion signal associated with the at least one axis signal;
detect a cardiac event from the motion signal after the expiration of the blanking period; and
a pulse generator configured to generate a pacing pulse in response to the circuitry detecting the cardiac event from the motion signal.

11. The medical device of claim 10, wherein:
the circuitry is further configured to:
detect the cardiac event by detecting an atrial event from the motion signal; and
set an atrioventricular pacing interval in response to detecting the atrial event; and
the pulse generator is configured to generate the pacing pulse at the atrioventricular pacing interval following the detected atrial event.

12. The medical device of claim 10, wherein:
the circuitry is further configured to identify a cardiac electrical event; and
the circuitry is further configured to:
start the blanking period in response to the cardiac electrical event; and
suspend the sampling of the at least one axis signal in response to starting the blanking period.

13. The medical device of claim 10, wherein the circuitry comprises a filter having a settling time and is further configured to restart the sampling of the at least one axis signal at the settling time earlier than the expiration time of the blanking period.

14. The medical device of claim 10, wherein the circuitry comprises a processor and is further configured to:
determine a feature of the motion signal between each of a predetermined number of the blanking periods;
wake up the processor after the predetermined number of blanking periods; and
the processor is configured to determine a cardiac event sensing control parameter used for detecting the cardiac event from the motion signal based on the determined features in response to being woken up.

15. The medical device of claim 10, wherein the circuitry is further configured to sample a second axis signal of the motion sensor, the motion signal associated with the at least one axis signal and the second axis signal.

16. The medical device of claim 15, wherein the circuitry is further configured to sample the second axis signal of the motion sensor throughout the blanking period.

17. The medical device of claim 16, wherein the circuitry is further configured to produce a patient physical activity signal associated with the second axis signal.

18. The medical device of claim 10, further comprising:
a housing that encloses the motion sensor, the circuitry and the pulse generator; and
at least one leadless electrode on the housing for delivering the generated pacing pulse.

* * * * *